US009981023B2

(12) United States Patent
Paulson et al.

(10) Patent No.: US 9,981,023 B2
(45) Date of Patent: May 29, 2018

(54) COMPOSITIONS AND METHODS FOR INDUCING IMMUNE TOLERANCE

(71) Applicant: The Scripps Research Institute, La Jolla, CA (US)

(72) Inventors: James C. Paulson, Del Mar, CA (US); Matthew MacAuley, San Diego, CA (US); David Nemazee, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days. days.

(21) Appl. No.: 15/370,313

(22) Filed: Dec. 6, 2016

(65) Prior Publication Data
US 2017/0165333 A1    Jun. 15, 2017

Related U.S. Application Data

(62) Division of application No. 13/261,580, filed as application No. PCT/US2011/001343 on Jul. 29, 2011, now Pat. No. 9,522,183.

(60) Provisional application No. 61/464,136, filed on Feb. 28, 2011, provisional application No. 61/400,610, filed on Jul. 31, 2010.

(51) Int. Cl.
*A61K 39/00* (2006.01)

(52) U.S. Cl.
CPC ........ *A61K 39/0008* (2013.01); *A61K 39/001* (2013.01); *A61K 2039/5154* (2013.01); *A61K 2039/5158* (2013.01); *A61K 2039/55555* (2013.01)

(58) Field of Classification Search
None
See application file for complete search history.

(56) References Cited

U.S. PATENT DOCUMENTS

| | | | |
|---|---|---|---|
| 8,357,671 B2 | 1/2013 | Paulson et al. | |
| 9,522,183 B2 * | 12/2016 | Paulson | A61K 39/001 |
| 2003/0118659 A1 | 6/2003 | August et al. | |
| 2010/0129392 A1 | 5/2010 | Shi et al. | |
| 2013/0164364 A1 | 6/2013 | Paulson et al. | |
| 2013/0171233 A1 | 7/2013 | Paulson et al. | |

FOREIGN PATENT DOCUMENTS

| | | |
|---|---|---|
| WO | WO-2007056525 A2 | 5/2007 |
| WO | WO-2010085509 A1 | 7/2010 |
| WO | WO-2012018380 A2 | 2/2012 |

OTHER PUBLICATIONS

Jellusova, et al. (2012) "Regulation of B cell functions b the sialic acid-binding receptors Siglec-G and CD22", Frontiers in Immunology, 2: Article 96, 14 pages.*

Angata, Yakashi, "Molecular diversity and evolution of the Siglec family of cell-surface lectins", Molecular Diversity, 10(4), (2006), 555-566.
Basten, Antony, et al., "B-cell tolerance: mechanisms and implications", Current Opinions in Immunology, 22(5), (2010), 566-574.
Blixt, Ola et al., "Sialoside Analogue Arrays for Rapid Identification of High Affinity Siglec Ligands", J. Am. Chem. Soc., 130(21), (2008), 6680-6681.
Chaouchi, Nadia, et al., "B Cell Antigen Receptor-Mediated Apoptosis: Importance of Accessory Molecules CD19 and CD22 and of Surface IgM Cross-Linking", The Journal of Immunology, 154(7), (1995), 3096-104.
Chen, Weihsu C, et al., "Antigen Delivery to Macrophages Using Liposomal Nanoparticles Targeting Sialoadhesin/CD169", PLoS One, 7(6), e39039, (2012), 1-9.
Courtney, Adam H., et al., "Sialylated multivalent antigens engage CD22 in trans and inhibit B cell activation", Proceedings of the National Academy of Science of the United States of America, 106(8), (Feb. 24, 2009), 2500-05.
Crocker, Paul R., et al., "Siglecs and their roles in the immune system", Nature Reviews Immunology, 7(4), (2007), 255-266.
Crocker, Paul R., et al., "Siglecs in the immune system", Immunology, 103(2), (2001), 137-145.
Duong, B. H, et al., "Decoration of T-independent antigen with ligands for CD22 and SiglecG can suppress immunity and induce B cell tolerance in vivo", Journal of Experimental Medicine, 207(1), (2010), 173-187.
Engel, P., et al., "The Same Epitope on CD22 of B Lymphocytes Mediates the Adhesion of Erythrocytes, T and B Lymphocytes, Neutrophils, and Monocytes", The Journal of Immunology, 150(11), (1993), 4719-4732.
Hitsumoto, Y., et al., "Induction of tolerance by haptenated liposomes carrying mouse erythrocyte membrane glycoprotein", Immunology, 53(4), (1984), 847-854.
Hoffmann, Anja, et al., "Siglec-G is a B1 cell-inhibitory receptor that controls expansion and calcium signaling of the B1 cell population", Nature Immunology, 8(7), (Jul. 2007), 695-704.
Kawasaki, Norihito, et al., "Targeted delivery of lipid antigen to macrophages via the CD169/sialoadhesin endocytic pathway induces robust invariant natural killer T cell activation", Proc. Natl. Acad. Sci. USA, 110(19), (May 2013), 7826-7831.
Kelm, S., et al., "The Ligand-binding Domain of CD22 Is Needed for Inhibition of the B Cell Receptor Signal, as Demonstrated by a Novel Human CD22-specific Inhibitor Compound", The Journal of Experimental Medicine, 195(9), (2002), 1207-1213.
Kodituwakku, Aruna P, et al., "Isolation of antigen-specific B cells", Immunology and Cell Biology (2003) 81, 163-170, (2003), 163-170.
Lanoue, Astrid, et al., "Interaction of CD22 with alpha2,6-linked sialoglycoconjugates: Innate recognition of self to dampen B cell autoreactivity?", European Journal of Immunology, 32(2), (2002), 348-355.

(Continued)

*Primary Examiner* — Robert M Kelly
(74) *Attorney, Agent, or Firm* — Schwegman, Lundberg & Woessner, P.A.

(57) ABSTRACT

The present invention provides liposomal compositions for inducing immune tolerance. The compounds typically comprise a liposome displaying a specific antigen and also a binding moiety for a sialic acid binding Ig-like lectin (Siglec) expressed on B cells. The invention also provides methods for inducing tolerance to a protein or polypeptide antigen (e.g., a protein antigen) in a subject. The methods involve administering to the subject a pharmaceutical composition thatco-presents both the antigen and a glycan ligand for a Siglec expressed on B lymphocytes.

8 Claims, 15 Drawing Sheets

(56) References Cited

OTHER PUBLICATIONS

MacAuley, Matthew S., et al., "Antigenic liposomes displaying CD22 ligands induce antigen-specific B cell apoptosis", Journal of Clinical Investigations, 123(7), (2013), 3074-3083.
Mihaylova, Nikolina, et al., "Simultaneous engagement of FcyIIb and CD22 inhibitory receptors silences targeted B cells and suppresses autoimmune disease activity", Molecular Immunology, 47(1), (2009), 123-130.
Nikolova, Kalina A., et al., "Selective silencing of autoreactive B lymphocytes—Following the Nature's way", (Abstract), Autoimmunity Rev., 9(11), 775-779, (2010), 1 pg.
Nitschke, Lars, "Suppressing the Antibody Response with Siglec Ligands", N Engl J Med 369:14, NEJM.org, (Oct. 3, 2013), 1373-1374.
O'Reilly, Mary K., et al., "Siglecs as targets for therapy in immune-cell-mediated disease", Trends in Pharmacological Sciences, 30(5), (2009), 240-248.
Pfrengle, Fabian, et al., "Copresentation of Antigen and Ligands of Siglec-G Induces B Cell Tolerance Independent of CD22", Journal of Immunology, 191(4), (Aug. 2013), 1724-1731.
Saul, Justin M., et al., "A dual-ligand approach for enhancing targeting selectivity of therapeutic nanocarriers", The Journal of Controlled Release, 114, (2006), 277-287.
Van Rossenberg, Sabine M., et al., "A Structure-Function Study of Ligand Recognition by CD22beta", J. Biol. Chem., 276(16), (2001), 12967-12973.
"Canadian Application Serial No. 2,807,141, Office Action dated Nov. 3, 2017", 3 pgs.
"European Application Serial No. 11814896.4, Response filed Sep. 22, 2017 to Office Action dated Jul. 14, 2017", 54pgs.

\* cited by examiner

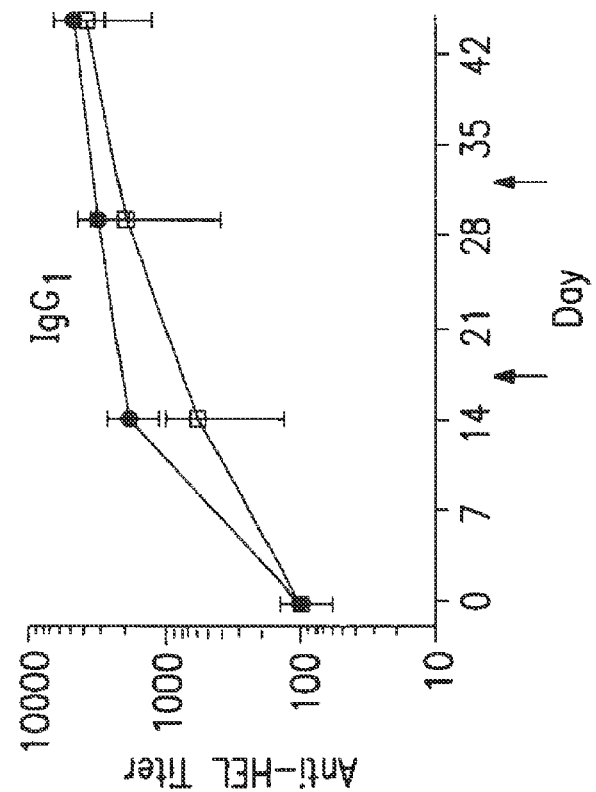
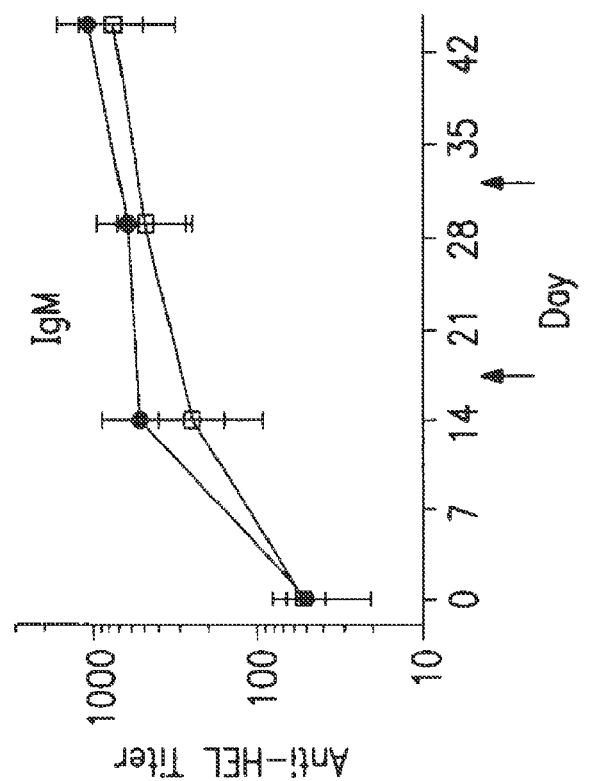
Fig. 3A
Fig. 3B

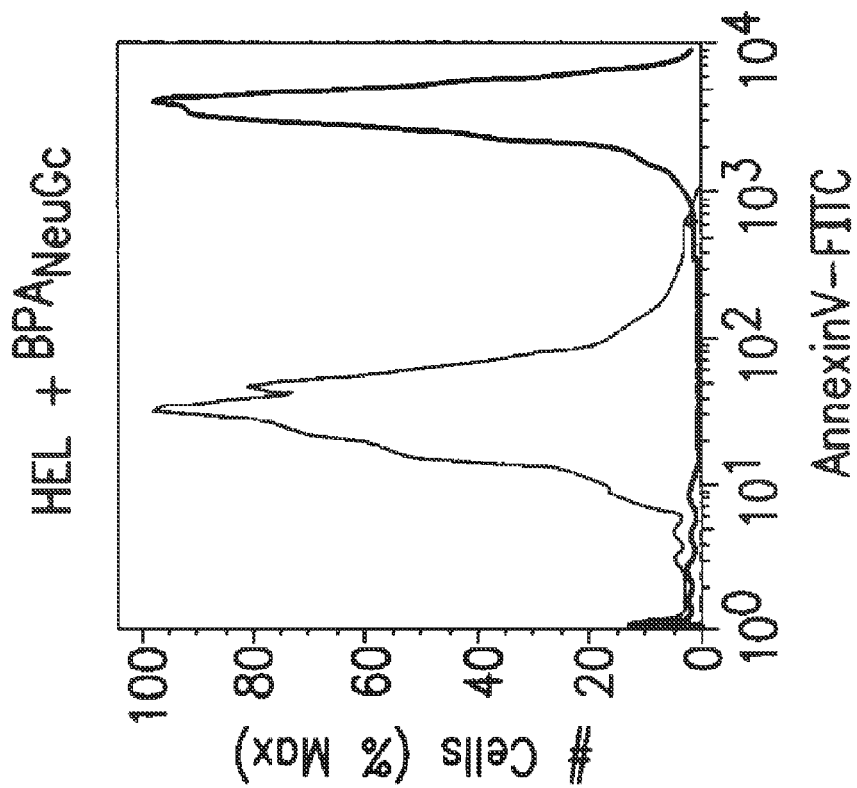
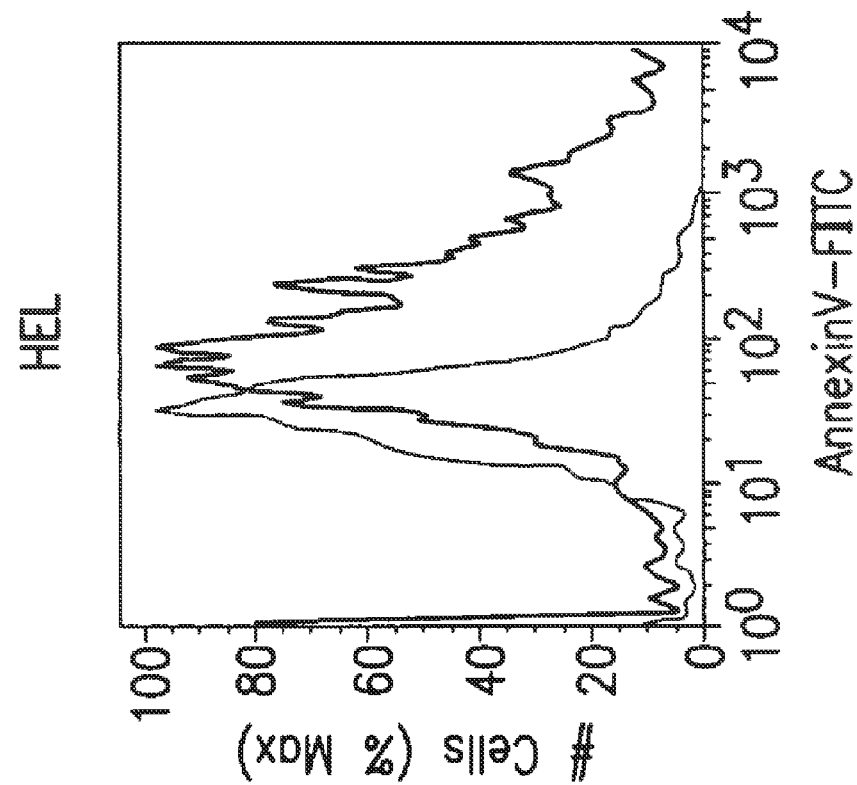
Fig. 5B
Fig. 5A

COMPOSITIONS AND METHODS FOR INDUCING IMMUNE TOLERANCE

CROSS-REFERENCE TO RELATED APPLICATIONS

This application is a continuation of U.S. patent application Ser. No. 13/261,580, filed on Mar. 8, 2013, and issued on Dec. 20, 2016 as U.S. Pat. 9,522,183, which is a U.S. National Stage Filing under 35 U.S.C. § 371 from International application No. PCT/US2011/001343, filed on Jul. 29, 2011, and published as WO2012/018380 on Feb. 9, 2012, which claims the benefit of priority to U.S. Provisional Application Ser. No. 61/464,136, filed on Feb. 28, 2011 and U.S. Provisional Application Ser. No. 61/400,610, filed on Jul. 31, 2010. The full disclosures of these priority applications are incorporated herein by reference in their entirety and for all purposes.

STATEMENT OF GOVERNMENT SUPPORT

This invention was made with government support under Contract Nos, GM060938, AI050143, and GM044809 awarded by the National Institutes of Health. The government has certain rights in this invention.

BACKGROUND OF THE INVENTION

Immune responses are necessary for protection against potentially pathogenic microorganisms. However, undesired immune activation can cause injurious processes leading to damage or destruction of one's own tissues. Undesired immune activation occurs, for example, in autoimmune diseases where antibodies and/or T lymphocytes react with self antigens to the detriment of the body's tissues. This is also the case in allergic reactions characterized by an exaggerated immune response to certain environmental matters and which may result in inflammatory responses leading to tissue destruction. This is also the case in rejection of transplanted organs which is significantly mediated by alloreactive T cells present in the host which recognize donor alloantigens or xenoantigens.

Immune tolerance is the acquired lack of specific immune responsiveness to an antigen to which an immune response would normally occur. Typically, to induce tolerance, there must be an exposure to a tolerizing antigen, which results in the death or functional inactivation of certain lymphocytes. This process generally accounts for tolerance to self antigens, or self-tolerance. Immunosuppressive agents are useful in prevention or reduction of undesired immune responses, e.g., in treating patients with autoimmune diseases or with allogeneic transplants. However, immunosuppressive agents can also cause systemic immune suppression, toxicity and even death due to opportunistic infections.

There is a need in the art for safer and more effective means for inducing immune tolerance, especially antigen-specific immune tolerance. The instant invention addresses this and other needs.

SUMMARY OF THE INVENTION

In one aspect, the invention provides liposomal compositions for inducing immune tolerance to specific antigens. The compositions typically contain a liposome nanoparticle which displays on its surface both a specific antigen and also a ligand or a binding moiety for a sialic acid binding Ig-like lectin (Siglec). In some preferred embodiments, the ligand or binding moiety is a glycan ligand for the Siglec. Some of the liposomal compositions contain a ligand or binding moiety for a Siglec expressed on B lymphocytes, e.g., Siglec-2 (CD22) or Siglec-G/10.

In some embodiments of the invention, the liposomal compositions are intended for targeting a Siglec expressed on human lymphocytes. In some of these embodiments, the employed Siglec glycan ligand is 9-N-biphenylcarboxyl-NeuAcα2-6Galβ1-4GlcNAc (6'-BPCNeuAc), NeuAcα2-6Galβ1-4GlcNAc or NeuAcα2-6Galβ1-4(6-sulfo)GlcNAc. The specific antigen against which immune tolerance is to be induced can be a protein. The antigen can also be a hapten, a carbohydrate, or a nucleic acid. In related aspects, pharmaceutical compositions and kits comprising the liposomal composition of the invention are also provided.

In a related aspect, the invention provides methods for inducing tolerance to a T-dependent antigen in a subject (e.g. a specific polypeptide or protein antigen). These methods entail administering to the subject a pharmaceutical composition that contains an effective amount of the antigen and a ligand for a Siglec expressed on B lymphocytes. In some embodiments, the antigen is conjugated to the Siglec ligand covalently or non-covalently. In some other embodiments, the antigen and the Siglec ligand are co-displayed on a liposome, Some embodiments are directed to inducing immune tolerance to an autoantigen, an allergen, or an alloantigen. In some embodiments, the employed Siglec ligand is a glycan ligand that specifically recognizes a Siglec expressed on B lymphocytes, e.g., CD22 or Siglec-G/10. Some preferred embodiments of the invention are directed to inducing immune tolerance in a human subject. In these embodiments, a Siglec ligand that specifically recognizes a human Siglec is used, e.g., 9-N-biphenylcarboxyl-NeuAcα2-6Galβ1-4GlcNAc (6'-BPCNeuAc), NeuAcα2-6Galβ1-4GlcNAc, or NeuAcα2-6Galβ1-4(6-sulfo)GlcNAc.

In another aspect, the invention provides methods for suppressing or preventing an undesired immune response to a specific antigen in a subject. The methods involve administering to the subject a pharmaceutical composition containing a liposome composition that displays both the antigen and a ligand for a sialic acid binding Ig-like lectin (Siglec). The Siglec can be one expressed on the surface of B lymphocytes or one expressed on the surface of other leukocytes such as monocytes or macrophages, In some embodiments, the antigen displayed on the liposomal composition is an autoantigen, an allergen, or an alloantigen. Some embodiments employ a glycan ligand that specifically recognizes a Siglec expressed on B cells, e.g., CD22 or Siglec-G/10. In some preferred embodiments, the subject to be treated is a human. Some of these embodiments employ a Siglec glycan ligand that recognizes human CD22 or Siglec-10, e.g., 9-N-biphenylcarboxyl-NeuAcα2-6Galβ1-4GlcNAc (6'-BPCNeuAc) or 9-N-biphenylcarboxyl-NeuAcα2-3Galβ1-4GlcNAc (3'-BPCNeuAc).

A further understanding of the nature and advantages of the present invention may be realized by reference to the remaining portions of the specification and claims.

DESCRIPTION OF THE DRAWINGS

FIG. 1A shows a graph of average IgM titers on various days after injection of the liposomes. FIG. 1B shows a graph of average $IgG_1$ titers on various days after injection of the liposomes, FIG. 1C shows a graph of average $IgG_{2a}$ titers on various days after injection of the liposomes. FIG. 1D shows a scatter plot of IgM titers determined on various days after injection of the liposomes. FIGS. 1E 1D shows a scatter plot of $IgG_1$ titers determined on various days after injection of the liposomes. FIGS. 1F 1D shows a scatter plot of $IgG_{2a}$ titers determined on various days after injection of the liposomes.

FIG. 2A shows a graph of serum titer of IgM antibodies to HEL on day 44 versus ligand concentration as the log of the % of the total molar content of lipids. FIG. 2B shows a graph of serum titer of $IgG_1$ antibodies to HEL on day 44 versus ligand concentration as the log of the % of the total molar content of lipids. FIG. 2C shows a graph of serum titer of $IgG_{2a}$ antibodies to HEL on day 44 versus ligand concentration as the log of the % of the total molar content of lipids.

FIGS. 3A-3D show that no tolerization to HEL is achieved when using liposomes co-presenting HEL and $^{BPA}$NeuGc or NeuGc in CD22 knockout mice. FIG. 3A shows a graph of anti-HEL IgM titers at various times after injection of HEL and $^{BPA}$NeuGc into CD22 knockout mice. FIG. 3B shows a graph of anti-HEL Ig $G_1$ titers at various times after injection of HEL and $^{BPA}$NeuGc into CD22 knockout mice. FIG. 3C shows a graph of anti-HEL IgM titers at various times after injection of HEL and NeuGc into CD22 knockout mice. FIG. 3D shows a graph of anti-HEL Ig $G_1$ titers at various times after injection of HEIL and NeuGc into CD22 knockout mice.

FIG. 4A shows flow cytometry results of CFSE-labeled B cells incubated with HEL alone for 2 days. FIG. 4B shows flow cytometry results of CFSE-labeled. B cells incubated with HEL and BPANeuGc for 2 days. FIG. 4C shows flow cytometry results of CFSE-labeled B cells incubated with HEL alone for 3 days. FIG. 4D shows flow cytometry results of CFSE-labeled B cells incubated with HEL and BPA-NeuGc for 3 days. FIG. 4E shows flow cytometry results of CFSE-labeled B cells incubated with HEL alone for 4 days. FIG. 4F shows flow cytometry results of CFSE-labeled B cells incubated with HEL and BPANeuGc for 4 days.

FIGS. 5A-5B show that co-presentation of $^{BPA}$NeuGc and HEL on liposomes causes apoptosis of HEL-specific B cells in vitro. HEL-specific B cells were purified from the spleen of MD4 mice. Liposomes (10 nM final concentration) displaying HEL alone (FIG. 5A) or HEL and BPANeuGc (FIG. 5B) were incubated with $2\times10^5$ cells. After two days of incubation, the extent of apoptosis was determined by staining the cells with AnnexinV-FITC and analysis by cytometry. FIG. 5A illustrates the percent of B cells stained with AnnexinV-FITC after incubation with HEL for two days. FIG. 5B illustrates the percent of B cells stained with AnnexinV-FITC after incubation with HEL and BPANeuGc for two days.

FIG. 6A shows the percent of CFSE-labeled B cells from spleens removed three days after injection of liposomes displaying HEL. FIG. 6B shows the percent of CFSE-labeled B cells from spleens removed three days after injection of liposomes displaying HEL and $^{BPA}$NeuGc. FIG. 6C shows the percent of CFSE-labeled B cells from spleens removed four days after injection of liposomes displaying HEL. FIG. 6D shows the percent of CFSE-labeled B cells from spleens removed four days after injection of liposomes displaying HEL and $^{BPA}$NeuGc.

FIG. 7A shows the average anti-NP IgM titer at various days since injection of liposomes displaying NP alone (filled circles) or $^{BPA}$NeuGc and NP (open squares). FIG. 7B shows the average anti-NP $IgG_1$ titer at various days since injection of liposomes displaying NP alone (filled circles) or $^{BPA}$NeuGc and NP (open squares). FIG. 7C shows a scatter plot of anti-NP IgM titers detected at various days since injection of liposomes displaying NP alone (filled circles) or $^{BPA}$NeuGc and NP (open squares). FIG. 7D shows a scatter plot of anti-NP $IgG_1$ titers detected at various days since injection of liposomes displaying NP alone (filled circles) or $^{BPA}$NeuGc and NP (open squares).

DETAILED DESCRIPTION

I. Overview

Figure 1A:
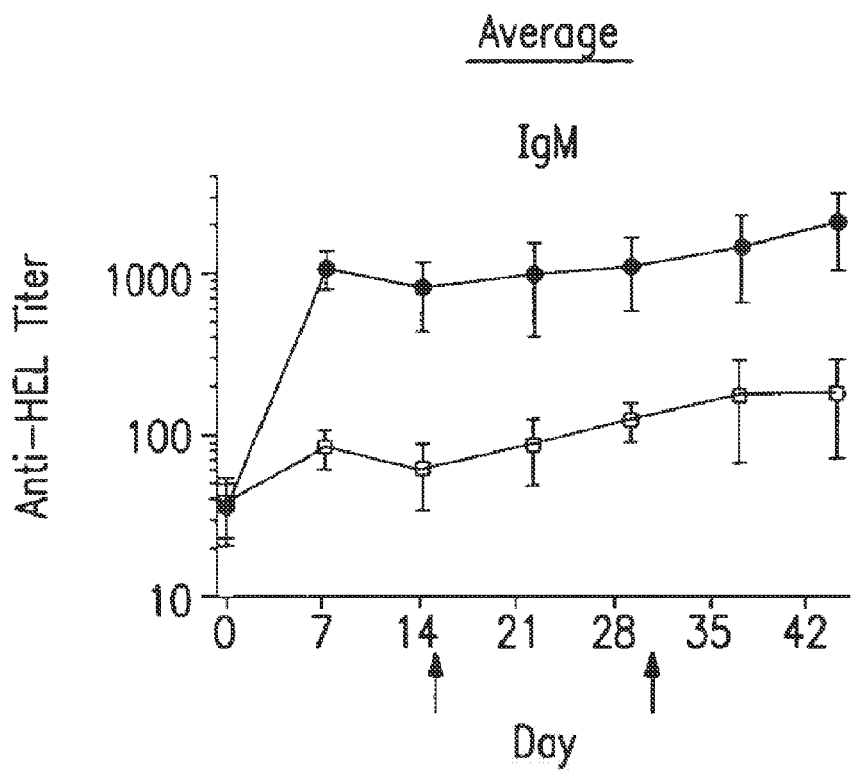
FIGS. 1A-1F show that liposomes displaying a synthetic glycan ligand of mouse CD 22, $^{BPA}$NeuGc, and hen egg lysozyme (HEL) induce tolerance to HEL in mice. Antibody titers were determined at various times after injection (on day 0) of 200 μL of liposomes (1.25 mM lipid) displaying HEL alone (filled circles) or $^{BPA}$NeuGc and HEL (open squares) into C57BL/6J mice (n=12 per group) via the lateral tail vein.
Figure 1B:
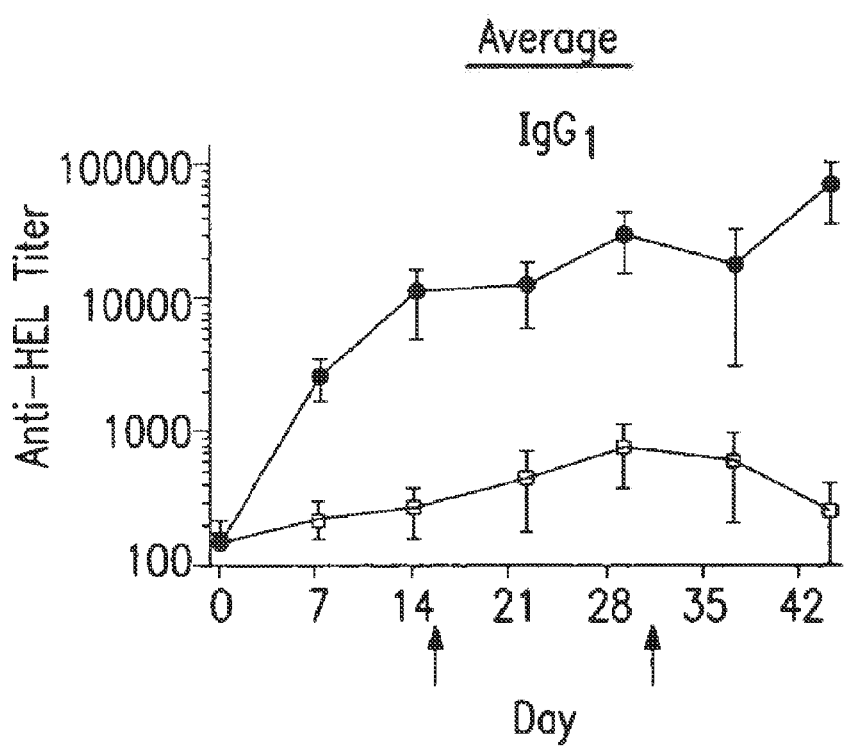
Figure 1C:
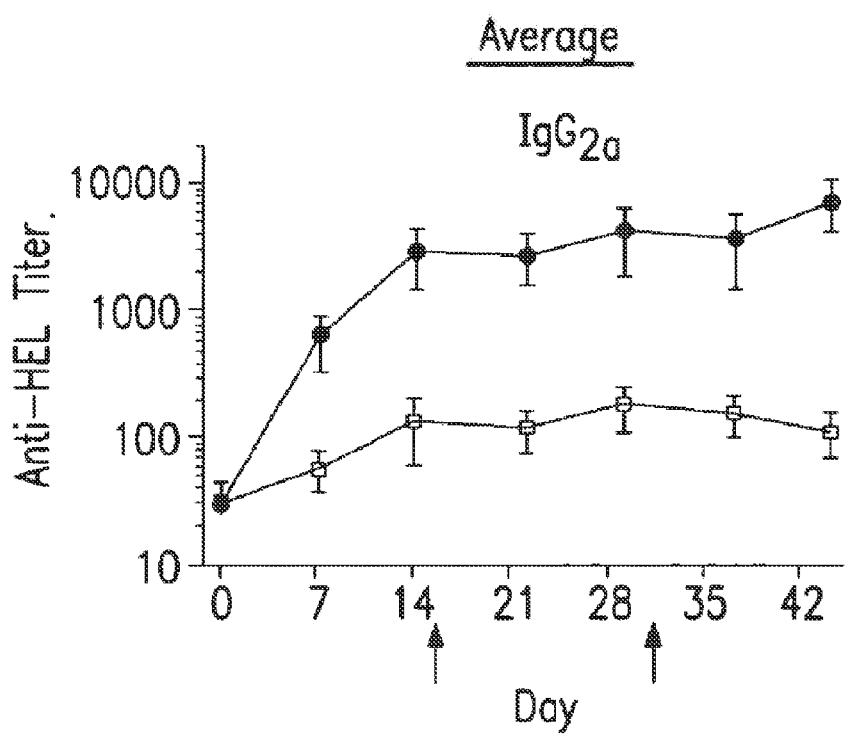
Figure 1D:
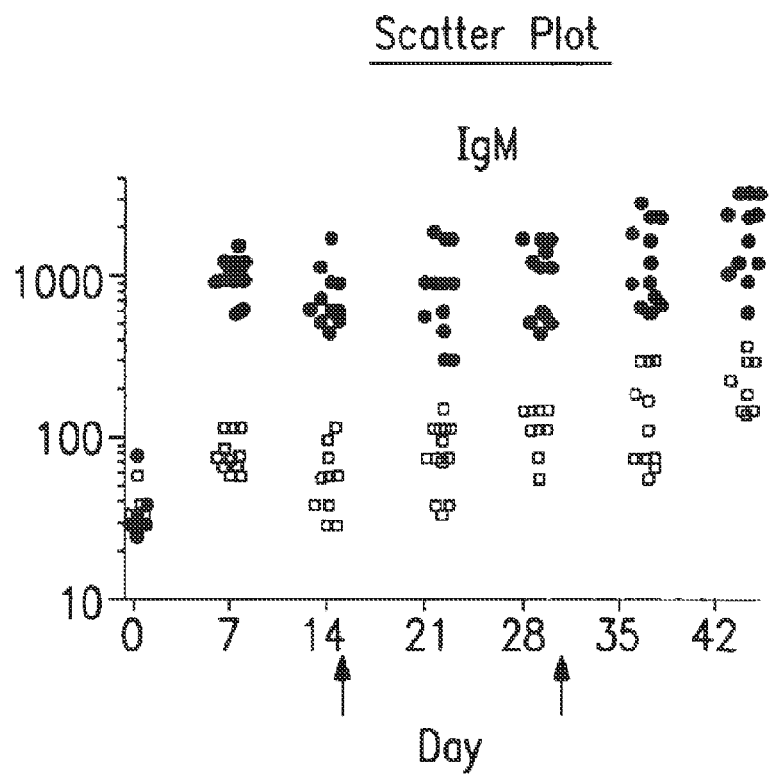
Figure 1E:
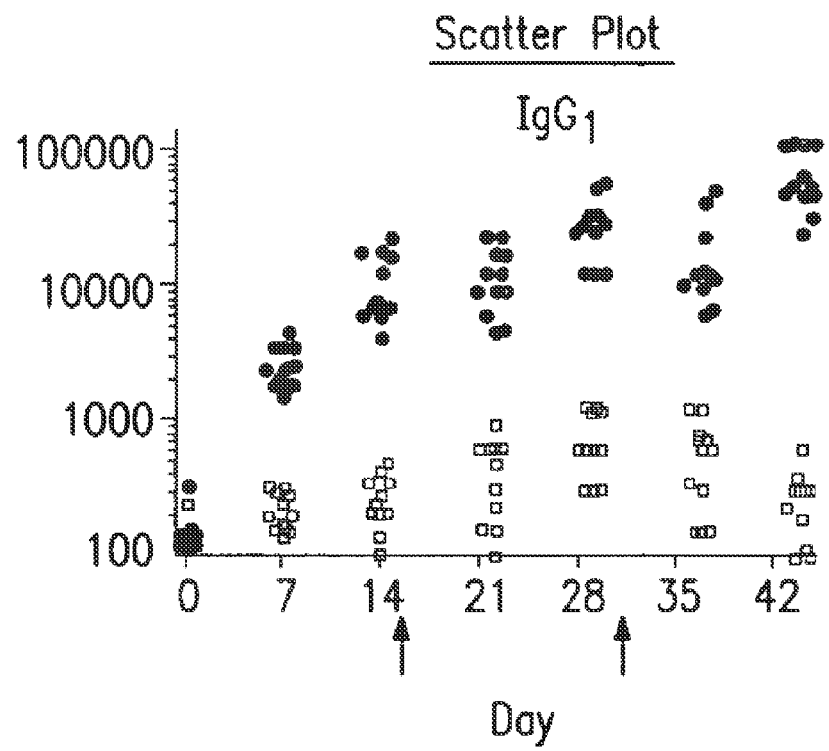
Figure 1F:
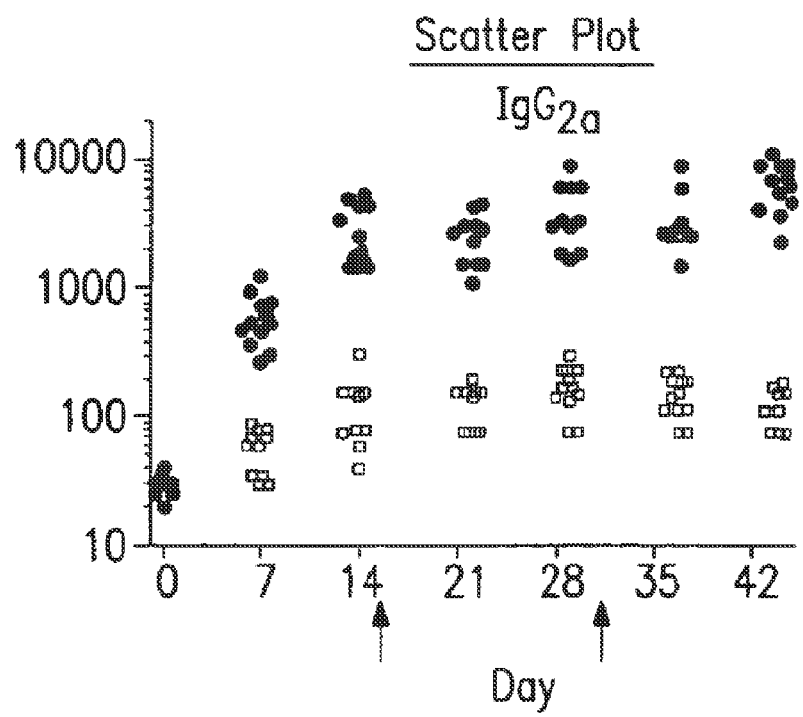

The present invention is predicated in part on the present inventors' discoveries that co-presentation of a T-dependent (protein) antigen with Siglec ligands can induce tolerance to the antigen. In addition, it was demonstrated that a liposomal formulation displaying an antigen and a Siglec ligand can induce tolerance to either a T-dependent (protein) or T-independent (hapten) antigen. Specifically, profound systemic B cell tolerance to an antigen (e.g., a T-dependent protein antigen or a T-independent small molecule hapten) was induced in animals by administration of liposomal nanoparticles that displays both the antigen and high affinity ligands of B cell Siglecs (CD22 and Siglec-G). Subsequent administration of antigen 15 or 30 days later results in a severely blunted production of antibody. It presence of the Siglec ligand on the antigen bearing liposome not only suppresses B cell activation, but also induces apoptosis of the cell that recognizes the antigen.

The present invention accordingly provides methods and compositions for suppressing undesired immune responses (e.g., autoimmune responses) and inducing systemic immune tolerance to any specific antigen. Some embodiments of the invention relate to suppressing immune responses and inducing tolerance to protein or polypeptide antigens by co-presenting a T cell-dependent antigen and a high affinity Siglec ligand. Some other embodiments relate to suppressing immune response and inducing tolerance to any specific antigen via a liposomal composition displaying both the antigen and a high affinity Siglec ligand. The invention also provides liposomal compositions bearing (or immune-conjugates harboring) a Siglec ligand and a specific antigen for inducing systemic tolerance to the antigen in a subject. The following sections provide more detailed guidance for practicing the invention.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology,* Morris (Ed.), Academic Press ($1^{st}$ ed., 1992); *Oxford Dictionary of Biochemistry and Molecular Biology,* Smith et al. (Eds.), Oxford University Press (revised. ed., 2000); *Encyclopaedic Dictionary of Chemistry,* Kumar (Ed.), Anmol Publications Pvt. Ltd. (2002); *Dictionary of Microbiology and Molecular Biology,* Singleton et al. (Eds.), John Wiley & Sons ($3^{rd}$ ed., 2002); *Dictionary Chemistry,* Hunt (Ed.), Routledge ($1^{st}$ ed., 1999); *Dictionary of Pharmaceutical Medicine,* Nahler (Ed.), Springer-Verlag Telos (1994); *Dictionary of Organic Chemistry,* Kumar and Anandand (Eds.), Anmol Publications Pvt. Ltd. (2002); and *A Dictionary of Biology* (*Oxford Paperback Reference*), Martin and Hine (Eds.), Oxford University Press ($4^{th}$ ed., 2000). Further clarifications of some of these terms as they apply specifically to this invention are provided herein.

The term "agent" includes any substance, molecule, element, compound, entity, or a combination thereof. It includes, but is not limited to, e.g., protein, polypeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

The term "analog" or "derivative" is used herein to refer to a molecule that structurally resembles a reference molecule (e.g., a known Siglec ligand) but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs to identify variants of known compounds having improved traits (such as higher binding affinity for a target molecule) is an approach that is well known in pharmaceutical chemistry.

The term antigen broadly refers to a molecule that can be recognized by the immune system. It encompasses proteins, polypeptides, polysaccharides, small molecule haptens, nucleic acids, as well as lipid-linked antigens (polypeptide- or polysaccharide-linked lipids.

T cell-dependent or T-dependent antigens refer to antigens which require T cell assistance in eliciting antibody production by B cells. Structurally these antigens are characterized by multiple antigenic determinants. Proteins or polypeptides are typical examples of T-dependent antigens that contain antigenic determinants for both B and T cells. With a T-dependent antigen, the first signal comes from antigen cross linking of the B cell receptor (BCR) and the second signal comes from co-stimulation provided by a T cell. T-dependent antigens contain antigenic peptides that stimulate the T cell. Upon ligation of the BCR, the B cell processes the antigen, releasing antigenic peptides that are presented on B cell Class II MHC to a special subtype of T cell called a Th2 cell. The Th2 cell then secretes potent cytokines that activate the B cell. These cytokines trigger B cell proliferation, induce the B cells to produce antibodies of different classes and with increased affinity, and ultimately differentiate into antibody producing plasma cells.

T cell-independent or T-independent (TI) antigens are antigens which can directly stimulate the B cells to elicit an antibody response, do not contain proteins, and cannot induce cell help. Typically, T-independent antigens have polymeric structures, e.g., the same antigenic determinant repeated many times. Examples of T-independent antigens include small molecule haptens, nucleic acids, carbohydrates and polysaccharides.

As used herein, immune tolerance (or simply "tolerance") is the process by which the immune system does not attack an antigen. It occurs in three forms: central tolerance, peripheral tolerance and acquired tolerance. Tolerance can be either "natural" or "self tolerance", where the body does not mount an immune response to self antigens, or "induced tolerance", Where tolerance to antigens can be created by manipulating the immune system. When tolerance is induced, the body cannot produce an immune response to the antigen. Mechanisms of tolerance and tolerance induction are complex and poorly understood. As is well known in the art (see, e.g., Basten et al., Curr. Opinion Immunol. 22:566-574, 2010), known variables in the generation of tolerance include the differentiation stage of the B cell when antigen is presented, the type of antigen, and the involvement of T cells and other leukocytes in production of cytokines and cofactors. Thus, suppression of B cell activation cannot be equated with immune tolerance. For example, while B cell activation can be inhibited by cross-linking CD22 to the BCR, the selective silencing of B cells does not indicate induction of tolerance. See, e.g., Nikolova et al., Autoimmunity Rev. 9:775-779, 2010; Mihaylova et al., Mol. Immunol. 47:123-130, 2009; and Courtney et al., Proc. Natl. Acad. Sci. 106:2500-2505, 2009.

The term "immune conjugate" as used herein refers to a complex in which a Siglec ligand is coupled to an antigen. The Siglec ligand can be coupled directly to the antigen via an appropriate linking chemistry. Alternatively, the Siglec ligand is linked indirectly to the antigen, e.g., via a third molecule such as a spacer or a lipid moiety on a liposome. The linkage between the antigen and the Siglec ligand can be either covalent or non-covalent.

A "liposomal composition" as used herein refers to a complex that contains a lipid component that forms a bilayer liposome structure, It is typically a semi-solid, ultra fine vesicle sized between about 10 and about 200 nanometers. The liposomal composition displays on or incorporates into the lipid moiety a binding moiety (e.g., a glycan ligand) that is specific for a target molecule (e.g., a Siglec) on a target cell. Typically, the binding moiety is integrated into the lipid component of the liposome complex. The liposomal composition additionally also displays a biological agent (e.g., an antigen) that is to be delivered to a target cell. The biological agent is typically also integrated into the lipid component of the liposome complex. Unless otherwise noted, the biological agent (e.g., an antigen) is not present in an aqueous solution encapsulated inside the lipid bilayer of the liposome.

Siglecs, short for sialic acid binding Ig-like lectins, are cell surface receptors and members of the immunoglobulin superfamily (IgSF) that recognize sugars. Their ability to recognize carbohydrates using an immunoglobulin domain places them in the group of I-type (Ig-type) lectins. They are transmembrane proteins that contain an N-terminal V-like immunoglobulin (IgV) domain that binds sialic acid and a variable number of C2-type Ig (IgC2) domains. The first described Siglec is sialoadhesin (Siglec-1/CD169) that is a lectin-like adhesion molecule on macrophages. Other Siglecs were later added to this family, including CD22 (Siglec-2) and Siglec-G/10 (i.e., human Siglec-10 and mouse Siglec-G), which is expressed on B cells and has an important role in regulating their adhesion and activation, CD33 (Siglec-3) and myelin-associated glycoprotein (MAG/Siglec-4). Several additional Siglecs (Siglecs 5-12) have been identified in humans that are highly similar in structure to CD33 so are collectively referred to as 'CD33-related Siglecs'. These Siglecs are expressed on human NK cells, B cells, and/or monocytes. CD33-related Siglecs all have two conserved immunoreceptor tyrosine-based inhibitory motif (ITIM)-like motifs in their cytoplasmic tails suggesting their involvement in cellular activation. Detailed description of Siglecs is provided in the literature, e.g., Crocker et al., Nat. Rev. Immunol. 7:255-66, 2007; Crocker et al., Immunol. 103:137-45, 2001; Angata et al., Mol. Diversity 10:555-566, 2006; and Hoffman et al., Nat. Immunol. 8:695-704, 2007.

Glycan ligands of Siglecs refer to compounds which specifically recognize one or more Siglecs and which comprise homo- or heteropolymers of monosaccharide residues. In addition to glycan sequences, the Siglec glycan ligands can also contain pegylated lipid moiety connected to the glycan via a linker. Examples of various Siglec glycan ligands are reported in the literature, e.g., Paulson et al., WO 2007/056525; and Blixt et al., J. Am. Chem. Soc. 130:6680-1, 2008.

Leukocytes refer to cells of the immune system which are involved in defending the body against both infectious disease and foreign materials. More specifically, the term as used in the invention refers to mononuclear leukocytes including lymphocytes, monocytes, and macrophages.

Administration "in conjunction with" one or more other therapeutic agents includes simultaneous (concurrent) and consecutive administration in any order.

The term "contacting" has its normal meaning and refers to combining two or more agents (e.g., polypeptides or small molecule compounds) or combining agents with cells. Contacting can occur in vitro, e.g., combining an agent with a cell or combining two cells in a test tube or other container. Contacting can also occur in vivo, e.g., by targeted delivery of an agent to a cell inside the body of a subject.

The term "subject" refers to any animal classified as a mammal, e.g., human and non-human mammals. Examples of non-human animals include dogs, cats, cattle, horses, sheep, pigs, goats, rabbits, and etc. Unless otherwise noted, the terms "patient" or "subject" are used herein interchangeably. Preferably, the subject is human.

The term "treating" or "alleviating" includes the administration of compounds or agents to a subject to prevent or delay the onset of the symptoms, complications, or biochemical indicia of a disease (e.g., an autoimmune disease), alleviating the symptoms or arresting or inhibiting further development of the disease, condition, or disorder. Subjects in need of treatment include those already suffering from the disease or disorder as well as those being at risk of developing the disorder. Treatment may be prophylactic (to prevent or delay the onset of the disease, or to prevent the manifestation of clinical or subclinical symptoms thereof) or therapeutic suppression or alleviation of symptoms after the manifestation of the disease.

III. Antigens for Inducing Immune Tolerance

The invention provides compositions and methods for inducing systemic tolerance to a specific antigen. Various antigens can be used in preparing liposomal compositions or immune-conjugates for inducing immune tolerance as disclosed herein. The antigens include various T cell-dependent antigens or T cell-independent antigens. In some embodiments, the employed antigen is one that is involved in an undesired immune reaction or response. In some embodiments, the employed antigen is any antigen to which an individual may be at risk of developing an undesired immune reaction or response. For example, some embodiments of the invention are directed to compositions and methods for inducing immune tolerance against autoantigens, alloantigens or allergens.

Antigens of different chemical nature are suitable for inducing immune tolerance with methods of the invention. They include polypeptides or proteins, haptens, carbohydrates, nucleic acids, peptides, polyethylene glycol, lipids (e.g., sterols excluding cholesterol, fatty acids, and phospholipids), polysaccharides, and gangliosides. The various antigens suitable for practicing the present invention may be isolated from their source using purification techniques known in the art or, more conveniently, may be produced using recombinant methods. For example, the antigens can be obtained through a number of methods known in the art, including isolation and synthesis using chemical and enzymatic methods, in certain cases, such as for many sterols, fatty acids and phospholipids, the antigenic portions of the molecules are commercially available. Antigens derived from infectious agents may be obtained using methods known in the art, for example, from native viral or bacterial extracts, from cells infected with the infectious agent, from purified polypeptides, from recombinantly produced polypeptides and/or as synthetic peptides.

Some embodiments of the invention are intended for inducing immune tolerance to various autoantigens. Autoantigens are known for a number of autoimmune diseases. For example, Grave's disease is characterized by production of autoantibodies to the thyroid-stimulating hormone receptor of the thyroid gland, Hashimoto's thyroiditis by autoantibodies and T cells to thyroid antigens (e.g., thyroid peroxidase), and type I diabetes by T cells and autoantibodies to β cell antigens (e.g, glutamic acid decarboxylase and insulin). Other examples of autoantigens involved in autoimmune diseases include, but are not limited to, cytochrome P450 antigens in Addison's disease, myelin proteins (e.g., myelin basic protein) in MS, uveal antigens in uveitis, gastric parietal cell antigens (e.g., $H^+$/ATPase, intrinsic factor) in pernicious anemia, transglutaminase in gluten enteropathy, myocardial cell proteins (e.g., myosin) in myocarditis and rheumatic heart disease, platelet antigens (e.g., GP IIb/IIIa) in idiopathic thrombocytopenic purpura, red blood cell membrane proteins in autoimmune hemolytic anemia, neutrophil membrane proteins in autoimmune neutropenia, basement membrane antigens (e.g., type IV collagen .alpha.3 chain) in Goodpasture's disease, intrahepatic bile duct/mitochondrial antigens (e.g., 2-oxoacid dehydrogenase complexes) for primary biliary cirrhosis, hepatocyte antigens (e.g., cytochrome P450, 206) for autoimmune hepatitis, acetylcholine receptors for myasthenia gravis, and desmogleins for pemphigus and other bullous diseases.

Some embodiments of the invention are directed to inducing tolerance against protein antigens that are normally self antigens, but which certain individuals lack owing to genetic deficiency and to which unwanted immune reactions occur upon replacement therapy. Examples of such antigens include blood coagulation factors VIII and IX in subjects with hemophilia. A and B (see, e.g. van Heiden et al., Haemophilia. 16:35-43, 2010; and DiMichele, Br J Haematol. 138:305-15, 2007), alpha-L-iduronidase in subjects with Hurler syndrome (see, e.g., Kakavanos et al., FEBS Lett. 580:87-92, 2006), and adenosine deaminase in subjects with adult-type adenosine deaminase deficiency (see, e.g., Bax et al., Eur. J. Haematol. 79:338-48, 2007).

Some embodiments of the invention are directed to inducing immune tolerance to allergens. Any allergen can be employed in the practice of the invention. For example, various allergens from food are suitable for practice of the invention. Example of such allergens include peanut allergen (e.g., Ara h I or Ara h II); walnut allergen (e.g., Jug r I); brazil nut allergen (e.g., albumin); shrimp allergen (e.g., Pen a I); egg allergen (e.g., ovomucoid); milk allergen (e.g., bovine β-lactoglobin); wheat gluten antigen (e.g., gliadin); and fish allergen (e.g., parvalbumins). In some embodiments, the employed allergen is a latex allergen such as Hey b 7 (Sowka et al., Eur. J. Biochem. 255:213-219, 1998). In addition to food allergens, other types of allergens can also be used in the practice of the invention. Examples of such allergens including, but not limited to, ragweed pollen allergen Antigen E (Amb a I) (Rafnar et al., J. Biol, Chem. 266:1229-1236, 1991), grass allergen Lol p 1 (Tamborini et al., Eur. J. Biochem. 249:886-894, 1997), major dust mite allergens Der pI and Der PII (Chua et al., J. Exp. Med 167:175-182, 1988; Chua et al., Int. Arch. Allergy Appl. Immunol. 91:124-129, 1990), domestic cat allergen Fel d I (Rogers et al., Mol, Immunol. 30:559-568, 1993), white birch pollen Bet vl (Breiteneder et al., EMBO J. 8:1935-1938, 1989), Japanese cedar allergens Cry j 1 and Cry j 2 (Kingetsu et al., Immunol. 99:625-629, 2000), and protein antigens from other tree pollen (Elsayed et al., Scand., J. Clin. Lab. Invest. Suppl. 204:17-31, 1991). Also suitable for the invention are protein antigens from grass pollen and known allergens from trees, including allergens from birch, juniper and Japanese cedar.

In some embodiments, the employed antigen for inducing immune tolerance is an alloantigen. Alloantigens are generally cellular antigens that vary in structure among individual members of a single species. Alloantigens from one individual can be recognized as foreign antigens by other members of the same species and are often the basis for graft rejection reactions. Examples of alloantigens include, but are not limited to major histocompatability complex (MHC) class I and class II antigens, minor histocompatability antigens, certain tissue-specific antigens, endothelial glycoproteins such as blood group antigens, and carbohydrate determinants.

IV. Siglec Ligands and Complexes with Antigens for Inducing Tolerance

The present invention provides immune-conjugates which contain a binding moiety (e. g., a Siglec ligand) that is directly or indirectly linked to a specific antigen. Some of the immune-conjugates are specifically designed for inducing immune tolerance to protein antigens or other T-dependent antigens. The invention also provides liposomal compositions (or liposome complexes) that are suitable for inducing immune tolerance or suppressing immune response to a specific antigen. The liposomal compositions typically display both the specific antigen and a binding moiety that specifically recognizes a Siglec on a target cell (e.g., B lymphocytes or monocytes). The specific antigen displayed on the liposomal compositions can be any antigen described herein, including any T-dependent or T-independent antigen known in the art. In addition, the binding moiety of the liposomal compositions or immune conjugates of the invention typically contains a ligand for the Siglec.

The Siglec ligands suitable for the invention include ligands for various Siglec molecules. Some preferred embodiments of the invention employ glycan ligands directed again Siglecs that are expressed on the surface of B lymphocytes. For example, the ligands can be natural or synthetic ligands that specifically recognize CD22 (Siglec-2) and/or Siglec G/10. CD22 from a number of species are known in the art. For example, amino acid sequences for human CD22 are disclosed in the National Center for Biotechnology Information (NCBI) database (http://www.ncbi.nlm.nih.gov/) at accession number NP 001762 (gi: 4502651) and also available in WO 2007/056525. Mouse CD22 is also characterized in the art, e.g., Torres et al., J. Immunol. 149:2641-9, 1992; and Law et al., J Immunol. 155:3368-76, 1995. Other than CD22, Siglec-G/10 is another Siglec expressed on the surface of B cells. Human Siglec-10 and its mouse ortholog Sialec-G are both well known and characterized in the art. See, e.g., Munday et al., Biochem. J. 355:489-497, 2001; Whitney et al., Eur. J. Biochem. 268:6083-96, 2001; Hoffman et al., Nat. Immunol. 8:695-704, 2007; and Liu et al, Trends Immunol. 30:557-61, 2009.

Various ligands of CD22 and Siglec-G/10 are known and suitable for the practice of the present invention. See, e.g. Paulson et al., WO 2007/05625; Chen et al., Blood 115: 4778-86, 2010; Blixt et al. J. Am. Chem. Soc. 130:6680-1, 2008; Kumari et al., Virol. J. 4:42, 2007; and Kimura et al., J. Biol. Chem. 282:32200-7, 2007. For example, natural ligands of human CE22 such as NeuAcα2-6Galβ1-4Glc-NAc, or NeuAcα2-6Galβ1-4(6-sulfo)GlcNAc can be used for targeting an antigen to human B cells. In addition, a number of synthetic CD22 ligands with improved activities are also available, e.g., 9-N-biphenylcarboxyl-NeuAcβ2-6Galβ1-4GlcNAc (6'-BPCNeuAc) and 9-N-biphenylcarboxyl-NeuAcα2-3Galβ1-4GlcNAc (3'-BPCNeuAc). More specific glycan ligands for human CD22 or Siglec-10 are described in the art, e.g., Blixt et al., J. Am. Chem. Soc. 130:6680-1, 2008; and Paulson et al., WO 2007/056525. Similarly, many glycan ligands for mouse CD22 have been reported in the literature. Examples include NeuGcα2-6Galβ1-4GlcNAc (NeuGc), 9-N-biphenylacetyl-NeuGcα2-6Galβ1-4GlcNAc ($^{BPA}$NeuGc), and NeuGcα2-3Galβ1-4GlcNAc. Some of these CD22 ligands are also known to be able to bind to Siglec-G/10. Other than the natural and synthetic Siglec ligands exemplified herein, one can also employ derivative or analog compounds of any of these exemplified glycan ligands in the practice of the invention.

Some embodiments of the present invention relate to liposomal compositions (or liposome targeting compositions or complexes) for inducing systemic immune tolerance to a specific antigen. Typically, the liposomal compositions display on the surface of a liposome both a specific antigen and a binding moiety that specifically recognizes a Siglec on a target cell (e.g., B cell or monocytes). The binding moiety is a molecule that recognizes, binds or adheres to a target molecule located in a cell, tissue (e.g. extracellular matrix), fluid, organism, or subset thereof. The binding moiety and its target molecule represent a binding pair of molecules, which interact with each other through any of a variety of molecular forces including, for example, ionic, covalent, hydrophobic, van der Waals, and hydrogen bonding, so that the pair have the property of binding specifically to each other. Specific binding means that the binding pair exhibit binding with each other under conditions where they do not bind to another molecule. In some preferred embodiments, the binding moiety present on the liposomal composition is a glycan ligand that specifically recognizes a Siglec (e.g., CD22 or Siglec-G/10) expressed on the surface of B cells. In addition to the binding moiety, the liposome compositions of the invention also bear or display a specific antigen against which immune tolerance is to be induced. Any antigens (including but not limited to T-dependent antigen or T-independent antigens) described herein or well known in the art can be employed in preparing the liposomal composition.

The liposome component of the compounds of the invention is typically a vesicular structure of a water soluble particle obtained by aggregating amphipathic molecules including a hydrophilic region and a hydrophobic region. While the liposome component is a closed micelle formed by any amphipathic molecules, it preferably includes lipids. For example, the liposomes of the invention exemplified herein contain phospholipids such as distearoyl phosphatidylcholine (DSPC) and polyethyleneglycol-distearoyl phosphoethanolamine (PEG-DSPE). Other phospholipids can also be used in preparing the liposomes of the invention, including dipalmitoylphosphatidylcholine (DPPC), dioleylphosphatidylcholine (DOPC) and dioleylphosphatidyl ethanol amine (DOPE), sphingoglycolipid and glyceroglycolipid. These phospholipids are used for making the liposome, alone or in combination of two or more or in combination with a lipid derivative where a non-polar substance such as cholesterol or a water soluble polymer such as polyethylene glycol has been bound to the lipid.

The liposomal compositions of the invention can be prepared in accordance with methods well known in the art. For example, incorporation of a Siglec ligand and an antigen on the surface of a liposome can be achieved by any of the routinely practiced procedures. Detailed procedures for producing a liposome nanoparticle bearing a binding moiety and an antigen are also exemplified in the Examples herein. These include liposomes bearing an incorporated glycan ligand (e.g., $^{BPA}$NeuGc) and also a specific antigen nitrophenyl or hen egg lysozyme). In addition to the methods and procedures exemplified herein, various methods routinely used by the skilled artisans for preparing liposomes can also be employed in the present invention. For example, the methods described in Chen et al., Blood 115:4778-86, 2010; and *Liposome Technology,* vol. 1, 2$^{nd}$ edition (by Gregory Gregoriadis (CRC Press, Boca Raton, Ann Arbor, London, Tokyo), Chapter 4, pp 67-80, Chapter 10, pp 167-184 and Chapter 17, pp 261-276 (1993)) can be used. More specifically, suitable methods include, but are not limited to, a sonication method, an ethanol injection method, a French press method, an ether injection method, a cholic acid method, a calcium fusion method, a lyophilization method and a reverse phase evaporation method. A size of the liposome of the present invention is not particularly limited, and typically is preferably between 1 to 200 nm and more preferably between 10 to 100 nm in average. The structure of the liposome is not particularly limited, and may be any liposome such as unilamella and multilamella. As a solution encapsulated inside the liposome, it is possible to use buffer and saline and others in addition to water.

Other than the liposomal compositions described above, some other embodiments of the invention relate to immune conjugates which contain a specific antigen linked to a ligand for a Siglec expressed on the surface of a target cell (e.g., B cell or monocytes). Such immune conjugates can also be readily employed for delivering the antigen to the target cell and accordingly inducing immune tolerance to the antigen. Some of the immune conjugates are intended to target a protein or polypeptide antigen via a glycan ligand that recognizes a Siglec (Siglec-2 or Siglec-G/10) expressed on the surface of B cells. Any protein antigen or T-dependent antigen can be used for preparing such immune conjugates, Suitable ligands for targeting the antigen to B cells are also described herein. Conjugating a protein or polypeptide to a small binding ligand can be performed in accordance with methods well known in the art. See, e.g., *Chemistry of protein conjugation and cross-linking,* Shan Wong, CRC Press (Boca Raton, Fla., 1991); and Bioconjugate techniques, 2$^{nd}$ ed., Greg T. Hermanson, Academic Press (London, UK, 2008).

V. Inducing Immune Tolerance via Siglec Ligand-Mediated Antigen Targeting

The invention provides methods and therapeutic uses for suppressing undesired immune responses and/or inducing immune tolerance to a specific antigen. The compositions described herein can be used for treating or preventing various diseases or disorders which are associated with or mediated by an undesired immune response or immune activation. By targeting a specific antigen to B cells and/or other leukocytes (e.g., monocytes and macrophage) in a subject in need of treatment, the liposomal compositions or immune-conjugates of the invention are suitable for treating or ameliorating the symptoms of autoimmune diseases, allergies, asthma, graft-versus-host reactions or graft rejection reaction.

Some embodiments of the invention are directed to inducing immune tolerance in a subject by using the liposomal compositions disclosed herein to target a specific antigen to B cells in a subject. The antigen can be any antigen against which an immune tolerance is desired. These include both T-dependent antigens (e.g., protein or polypeptide antigens) and T-independent antigens (e.g., haptens or polysaccharides). In some other embodiments of the invention, immune tolerance against a protein or polypeptide antigen is induced by targeting to B cells an immune conjugate described herein which contains both a Siglec ligand and the specific antigen. In various embodiments, the liposome compositions or immune conjugates can be used for delivering an antigen to B cells either in vitro or in vivo. Preferably, the liposomal composition or immune conjugate bearing both the Siglec ligand and the specific antigen is administered to a. subject in vivo. By inducing immune tolerance and suppressing undesired immune response, the methods and compositions described herein find uses in the treatment of various diseases and disorders. In any of these applications, the liposome compositions or immune conjugates disclosed herein can be used alone or administered in conjunction with other known drugs in the treatment of a specific disease or condition. The invention further provides for a pharmaceutical combination (e.g., a kit) for carrying out these therapeutic applications. Such pharmaceutical combination can contain a liposomal composition or immune conjugate disclosed herein, in free form or in a composition, an optional co-agent or carrier, as well as instructions for administration of the agents.

The liposomal compositions or immune conjugates described herein can be administered alone or as a component of pharmaceutical compositions. Pharmaceutical compositions of the invention comprise an effective amount of the liposomal compositions or immune conjugates formulated with at least one pharmaceutically acceptable carrier. Pharmaceutical compositions of the invention can be prepared and administered to a subject by any methods well known in the art of pharmacy. See, e.g., *Goodman & Gilman's The Pharmacological Bases of Therapeutics*, Hardman et al., eds., McGraw-Hill Professional ($10^{th}$ ed., 2001); *Remington: The Science and Practice of Pharmacy*, Gennaro, ed., Lippincott Williams & Wilkins ($20^{th}$ ed, 2003); and *Pharmaceutical Dosage Forms and Drug Delivery Systems*, Ansel et al. (eds.), Lippincott Williams & Wilkins ($7^{th}$ ed., 1999). In addition, the pharmaceutical compositions of the invention may also be formulated to include other medically useful drugs or biological agents.

In some preferred embodiments, the liposomal compositions or immune conjugates are used for in vivo applications. In these applications, the liposome complexes set forth herein can be administered to a subject in need of treatment according to protocols already well established in the art. The liposomal compositions or immune conjugates can be administered alone or in combination with a carrier in an appropriate pharmaceutical composition. Typically, a therapeutically effective amount of the liposomal compositions or immune conjugates is combined with a pharmaceutically acceptable carrier. The pharmaceutically acceptable carrier is any carrier known or established in the art. Exemplary pharmaceutically acceptable carriers include sterile pyrogen-free water and sterile pyrogen-free saline solution. Other forms of pharmaceutically acceptable carriers that can be utilized for the present invention include binders, disintegrants, surfactants, absorption accelerators, moisture retention agents, absorbers, lubricants, fillers, extenders, moisture imparting agents, preservatives, stabilizers, emulsifiers, solubilizing agents, salts which control osmotic pressure, diluting agents such as buffers and excipients usually used depending on the use form of the formulation. These are optionally selected and used depending on the unit dosage of the resulting formulation.

A therapeutically effective amount of the antigen varies depending upon the disorder that a subject is afflicted with, other known factors of the subject such as age, weight, etc., and thus must be determined empirically in each case. This empirical determination can be made by routine experimentation. Typically, though, the liposome components may be used at a ratio of about 200:1 w/w, e.g., 100-300:1 w/w, compared to the antigen delivered. A typical therapeutic dose of the liposome composition is about 5-100 mg per dose, e.g., 10 mg per dose. For any given condition or disease, one can prepare a suitable liposomal composition which contains an appropriate amount of Siglec ligand and an appropriate antigen in accordance with the present disclosure and knowledge well known in the art , e.g., Springhouse, *Physician's Drug Handbook*, Lippincott Williams & Wilkins ($12^{th}$ edition, 2007).

For in vivo applications, the liposomal compositions or immune conjugates can be administered to the patient by any customary administration route, e.g., orally, parenterally or by inhalation. As shown in the Example below, a liposome co-displaying an antigen and a Siglec ligand can be administered to a subject by intravenous injection. In some other embodiments, the liposome complex can be administered to a subject intravascularly. A liposome useful for intravascular administration can be a small unilamellar liposome, or may be a liposome comprising PEG-2000. When the composition is parenterally administered, the form of the drug includes injectable agents (liquid agents, suspensions) used for intravenous injection, subcutaneous injection, intraperitoneal injection, intramuscular injection and intraperitoneal injection, liquid agents, suspensions, emulsions and dripping agents.

In some other embodiments, the liposomal composition or immune conjugate is administered orally to a subject. In these embodiments, a form of the drug includes solid formulations such as tablets, coated tablets, powdered agents, granules, capsules and pills, liquid formulations such as liquid agents (e.g., eye drops, nose drops), suspension, emulsion and syrup, inhales such as aerosol agents, atomizers and nebulizers, and liposome inclusion agents. In still some other embodiments, the liposome composition is administered by inhalation to the respiratory tract of a patient to target the trachea and/or the lung of a subject. In these embodiments, a commercially available nebulizer may be used to deliver a therapeutic dose of the liposome complex in the form of an aerosol.

The invention also provides kits useful in therapeutic applications of the compositions and methods disclosed herein. Typically, the kits of the invention contain one or more liposomal compositions or immune conjugates described herein. The kits can further comprise a suitable set of instructions, generally written instructions, relating to the use of the compounds for inducing immune tolerance to a specific antigen present in the compounds. The liposomal composition or immune conjugate can be present in the kits in any convenient and appropriate packaging. The instructions in the kits generally contain information as to dosage, dosing schedule, and route of administration for the intended method of use. The containers of kits may be unit doses, bulk packages (e.g., multi-dose packages) or sub-unit doses. instructions supplied in the kits of the invention are typically written instructions on a label or package insert (e.g., a paper sheet included in the kit), but machine-readable instructions (e.g., instructions carried on a magnetic or optical storage disk) are also acceptable.

In some embodiments, kits of the invention comprise materials for production of a liposomal composition or immune conjugate comprising a specific antigen and a Siglec ligand. Generally, these kits contain separate containers of one or more antigens and one or more Siglec ligands from which a liposomal composition or immune conjugate can be made. Additional regents for making the compounds can also be provided in the kits, e.g., reagents for making liposome. The Siglec ligands and the antigens are preferably supplied in a form which allows formation of complexes upon mixing of the other reagents with the supplied Siglec ligand and antigen.

EXAMPLES

The following examples are offered to illustrate, but not to limit the present invention. The studies exemplified herein were all performed in accordance with procedures that have been previously described. See, e.g., Paulson et al., U.S. Patent Application Publication No. 20090238837; Duong et al., J. Exp. Med. 207:173, 2010; Chen et al., Blood 115: 4778-86, 2010; and Reulen et al. Bioconjugate Chem., 21:860-866, 2010.

We examined whether liposomes displaying a synthetic glycan ligand of mouse CD22, $^{BPA}$NeuGc, and hen egg lysozyme (HEL) can induce tolerance to HEL in mice. The results are shown in FIGS. 1A-1F. On day 0, 200 μL of liposomes (1.25 mM lipid) displaying HEL alone (filled circles) or $^{BPA}$NeuGc and HEL (open squares) were injected into C57BL/6J mice (n=12 per group) via the lateral tail vein. On various days, the mice were bled and the anti-HEL titer (IgM, IgG$_1$, and IgG$_{2a}$ isotypes) was determined by an ELISA assay. On days 15 and 30 of the experiment (indicated with the arrows), both groups were challenged with the same quantity of liposomes displaying HEL alone. Shown on the left are average values and on the right a scatter plot containing each individual data point. Except for day 0, the p value between the two groups is less than 0.0001.

Figure 2A:
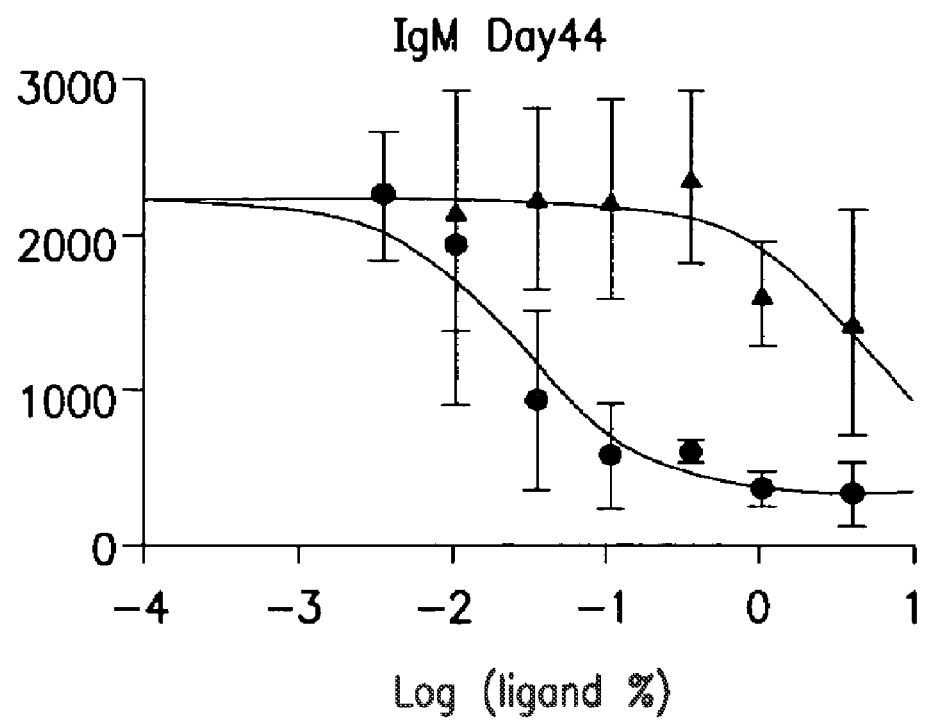
FIGS. 2A-2C show that liposomes displaying HEL, and a low affinity natural ligand of mouse CD22 can also induce tolerance to HEL in mice. Titers were determined at day 44 after injection of 200 µL of liposomes (1.25 mM lipid) displaying HEL (filled circles) and varying amounts of either $^{BPA}$NeuGc (closed circles) or the natural ligand of CD22, NeuGcα26Galβ14GlcNAc (closed triangles) into C57BL/6J mice (n=6 per group) via the lateral tail vein.
Figure 2B:
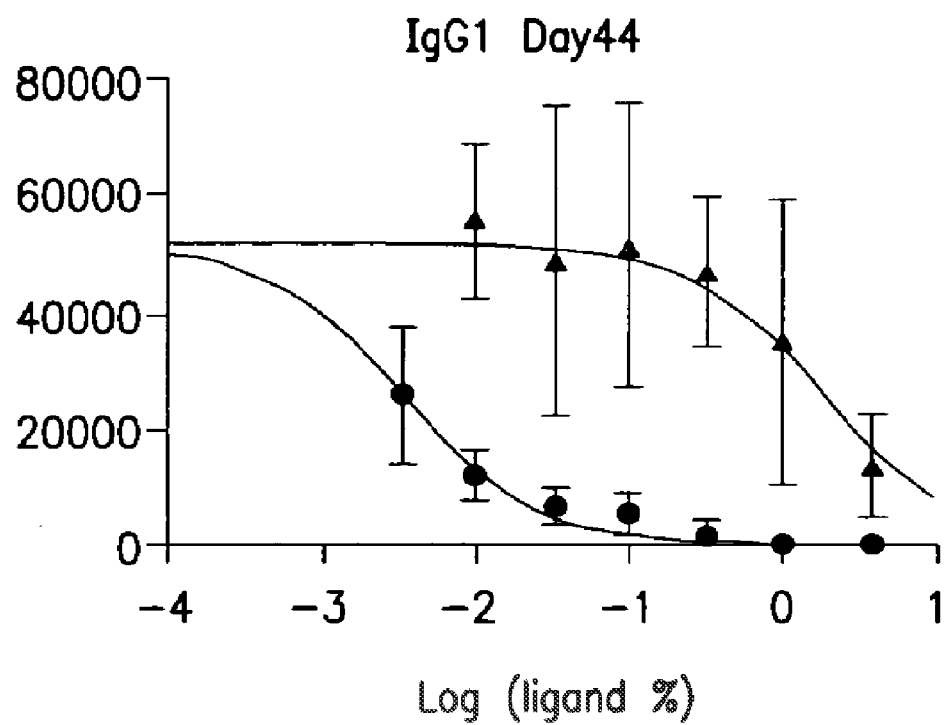
Figure 2C:
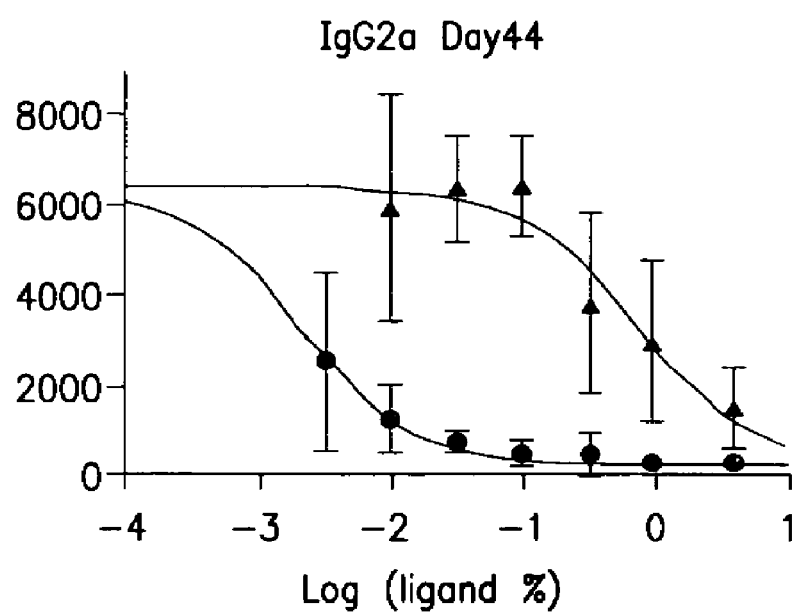
Figure 3D:
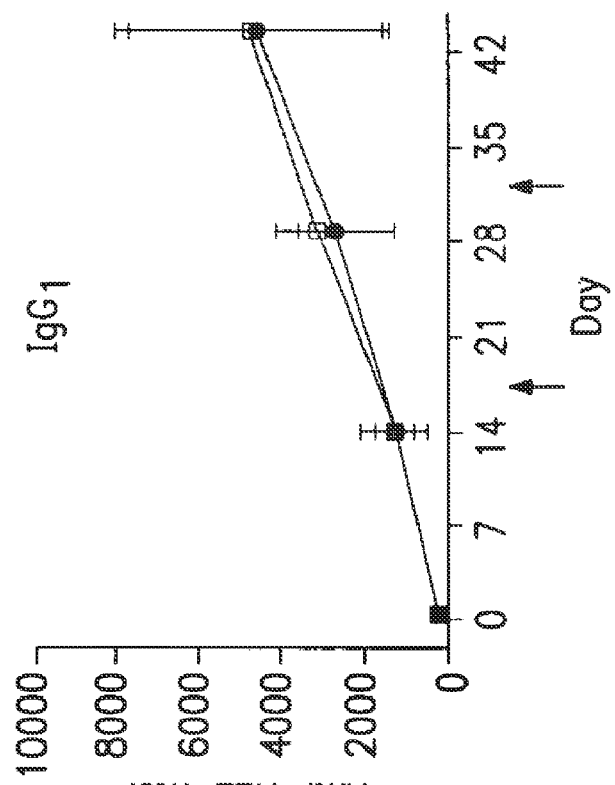
Figure 3C:
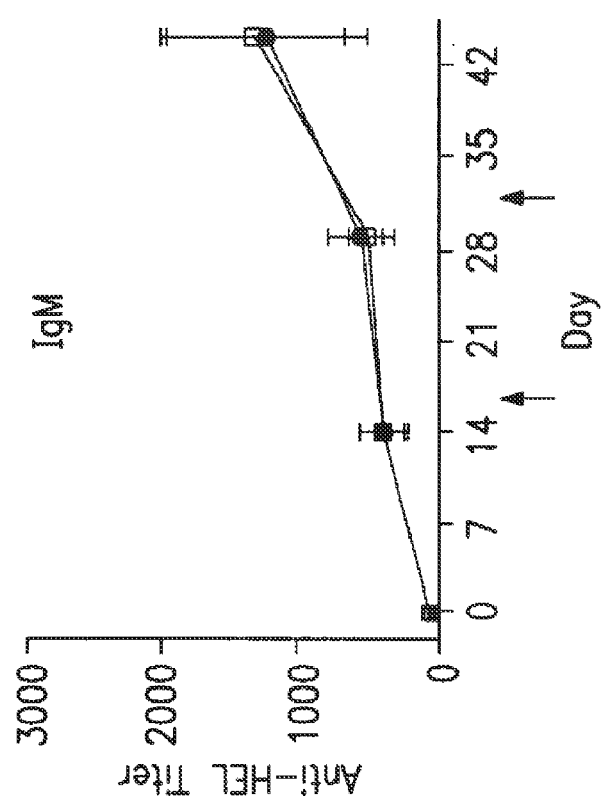

We then investigated the amount of Siglec ligand in the liposome formulation that is required to induce tolerance to hen egg lysozyme. Data obtained from the study are shown in FIGS. 2A-2C. The experiment is essentially the same as described for FIGS. 1A-1F except that multiple liposome formulations that differed in the type and amount of Siglec ligand were compared. On day 0, 200 μL of liposomes (1.25 mM lipid) displaying HEL (filled circles) and varying amounts of either $^{BPA}$NeuGc (closed circles) or the natural ligand of CD22, NeuGcα2-6Galβ1-4GlcNAc (closed triangles) were injected into C57BL/6J mice (n=6 per group) via the lateral tail vein. The ligand concentration in each preparation is shown as the log of the % of the total molar content of lipids, ranging from a 4% to about 0.003%. On days 15 and 30 of the experiment, both groups were challenged with the same quantity of liposomes displaying HEL alone. Shown are the serum titer of antibodies to HEL on day 44 (IgM, IgG$_1$, and IgG$_{2a}$ isotypes). Some tolerization is seen even at the lowest doses of the $^{BPA}$NeuGc ligand for IgG$_1$ and IgG$_{2a}$. Tolerization is also seen with the natural ligand of CD22 at the highest concentrations, even though it exhibits an affinity approximately 200 fold lower than the $^{BPA}$NeuGc ligand.

To investigate if this tolerization is CD22 dependent, we repeated the analogous studies with liposomes displaying either 0.3% $^{BPA}$NeuGc (FIGS. 3A and 3B) or 4% NeuGc (FIGS. 3C-3D) in CD22 knockout mice. As shown in FIGS. 3A-3D, no tolerance was observed in either case. These results clearly demonstrate that these ligands act through CD22.

Figure 4B:
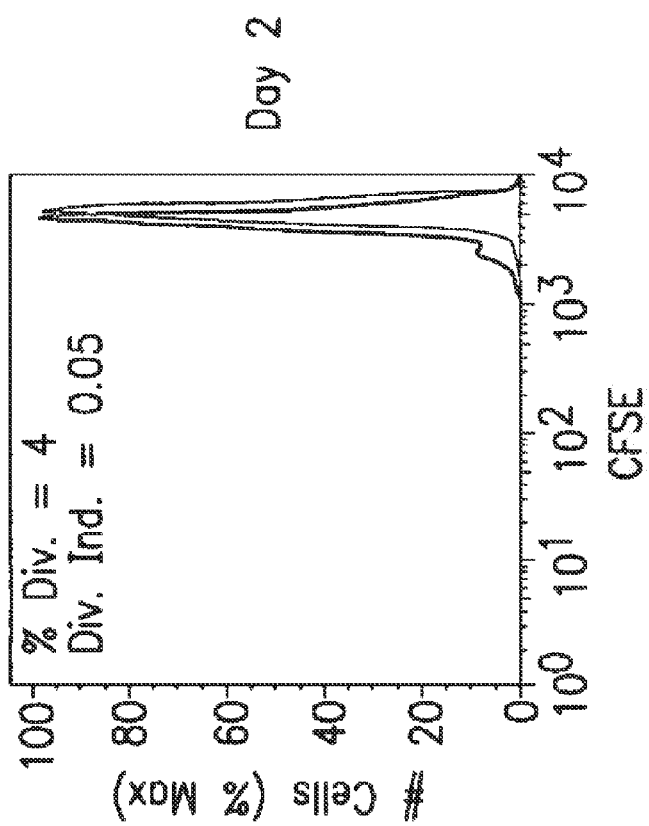
FIGS. 4A-4F show that co-presentation of $^{BPA}$NeuGc and HEL on liposomes greatly reduces the proliferation of HEL-specific B cells in vitro, HEL-specific B cells were purified from the spleen of MD4 mice and fluorescently labeled with carboxyfluorescein succinimidyl ester (CFSE). Liposomes (10 nM final concentration) displaying HEL alone (FIGS. 4A, 4C, 4E) or HEL and BPANeuGc (FIGS. 4B, 4D, 4F) were incubated with $2\times10^5$ of the B cells.
Figure 4A:
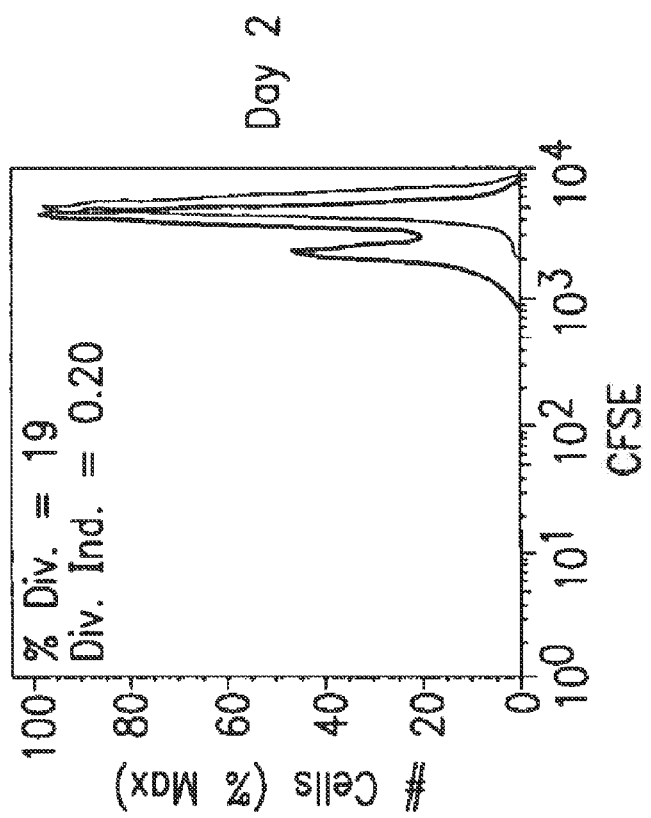
Figure 4D:
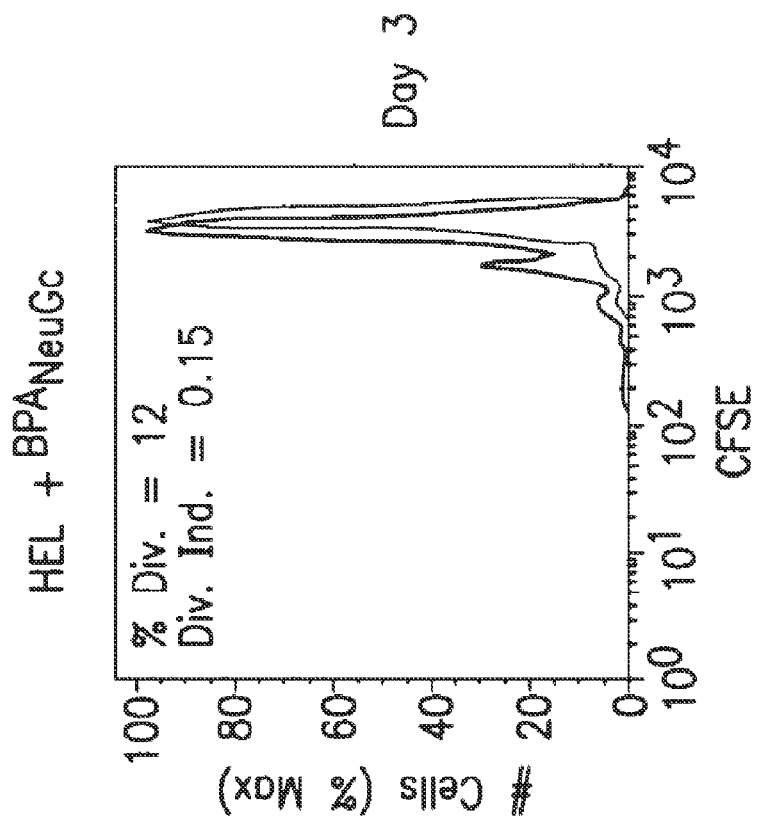
Figure 4C:
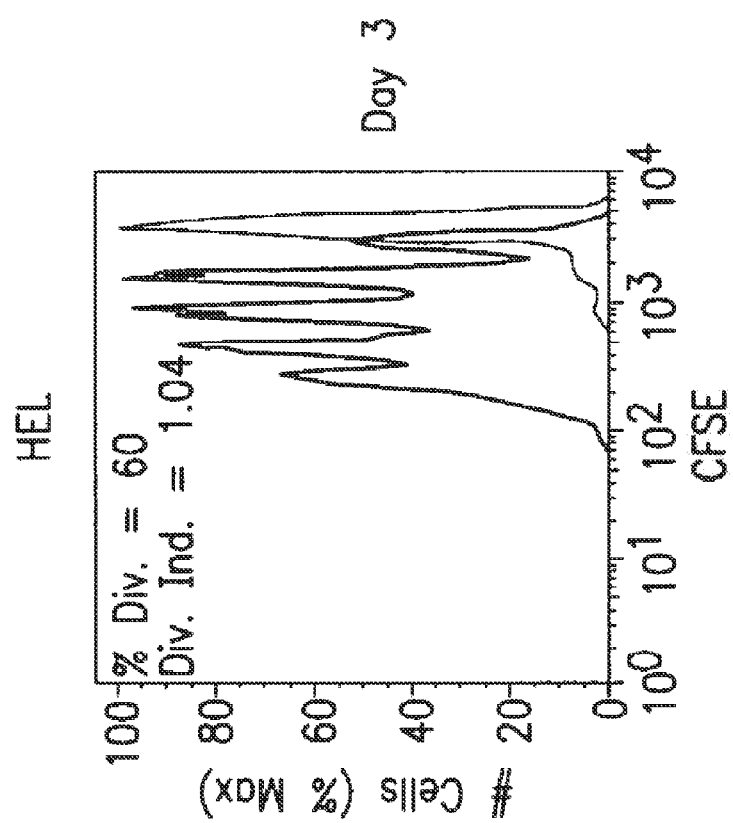
Figure 4F:
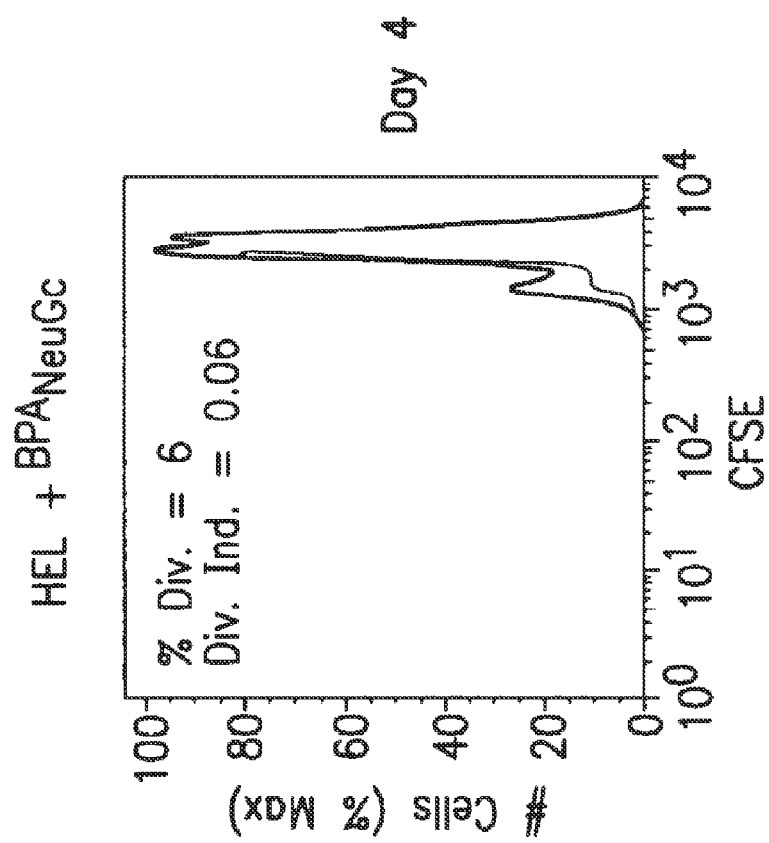
Figure 4E:
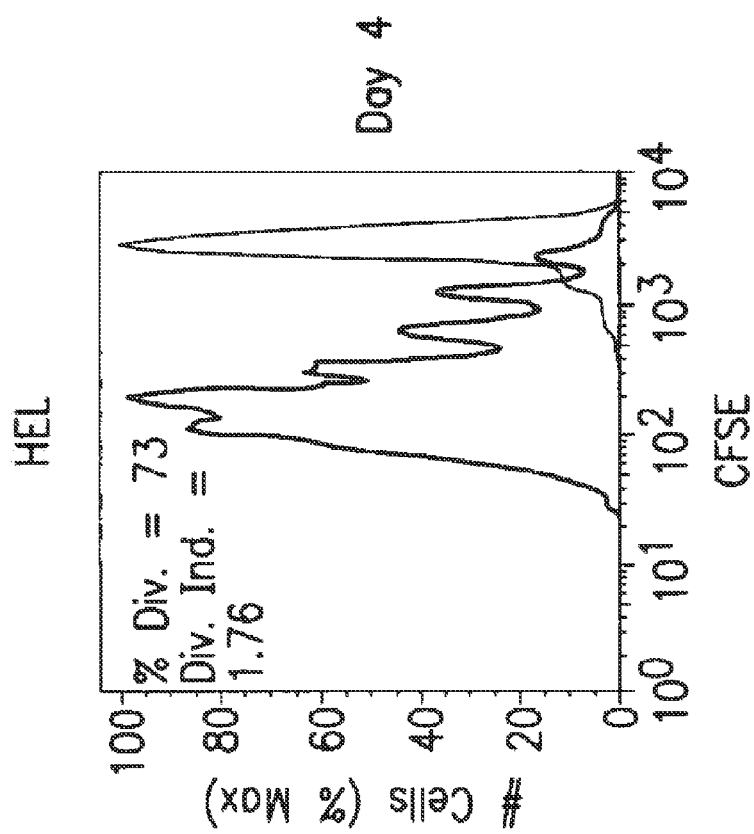
Figure 6A:
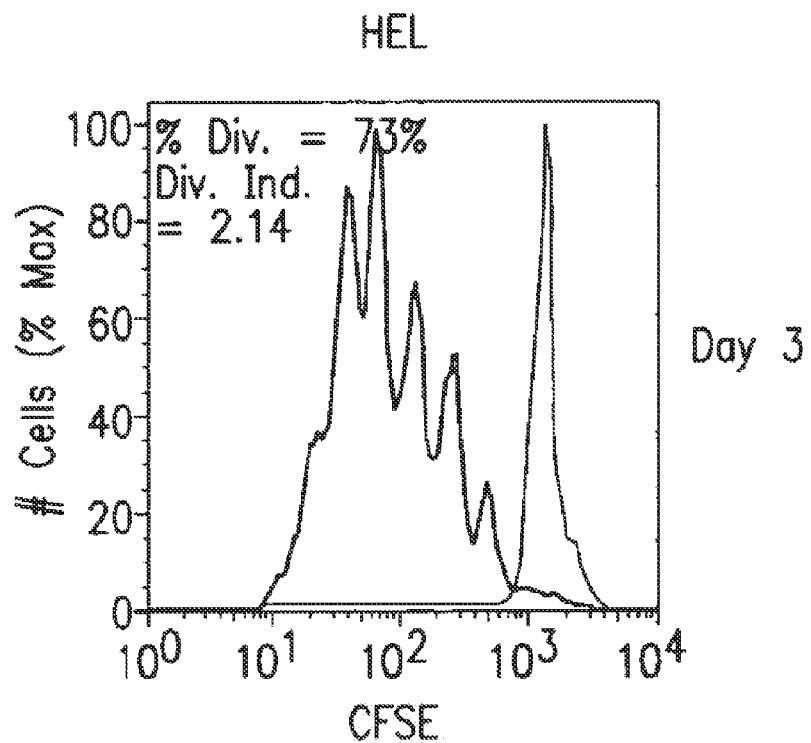
FIGS. 6A-6D show that co-presentation of $^{BPA}$NeuGc and HEL on liposomes greatly reduces the proliferation of HEL-specific B cells in vivo. HEL-specific B cells were purified from the spleen of MD4 mice (wild-type or CD22 knockout background) and fluorescently labeled with carboxyfluorescein succinimidyl ester (CFSE). Labeled cells ($8\times10^6$ or $5\times10^6$) were transferred into a host C57BL/6J mouse via the tail vein. Two hours later, liposomes displaying HEL alone or HEL and $^{BPA}$NeuGc were injected via the tail vein. On day 3 or 4, the spleen was removed and dilution of CFSE signal in splenocytes was determined by flow cytometry. HEL-specific B cells were gated for by staining with an anti-IgM$^A$-PE antibody.
Figure 6B:
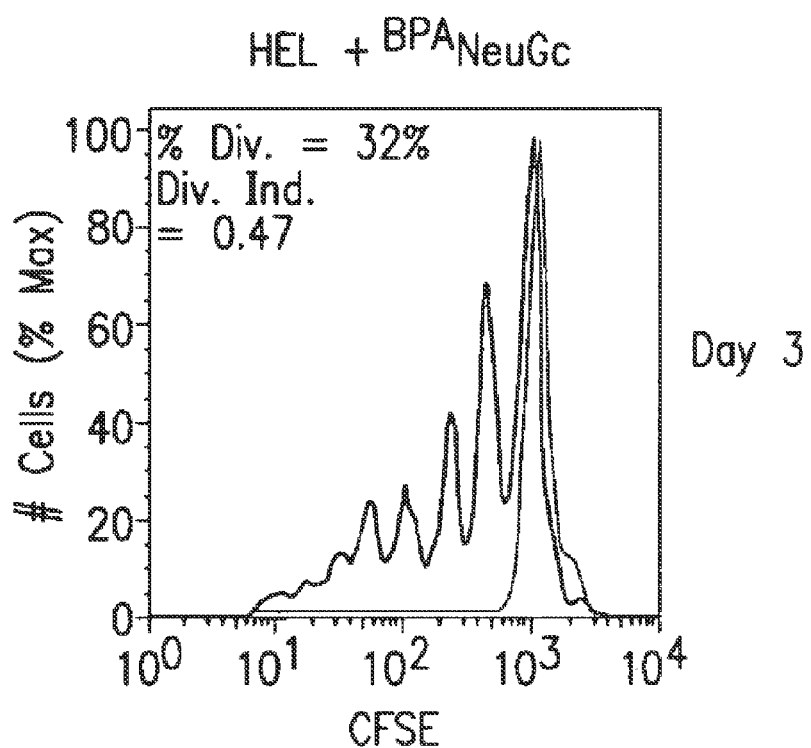
Figure 6C:
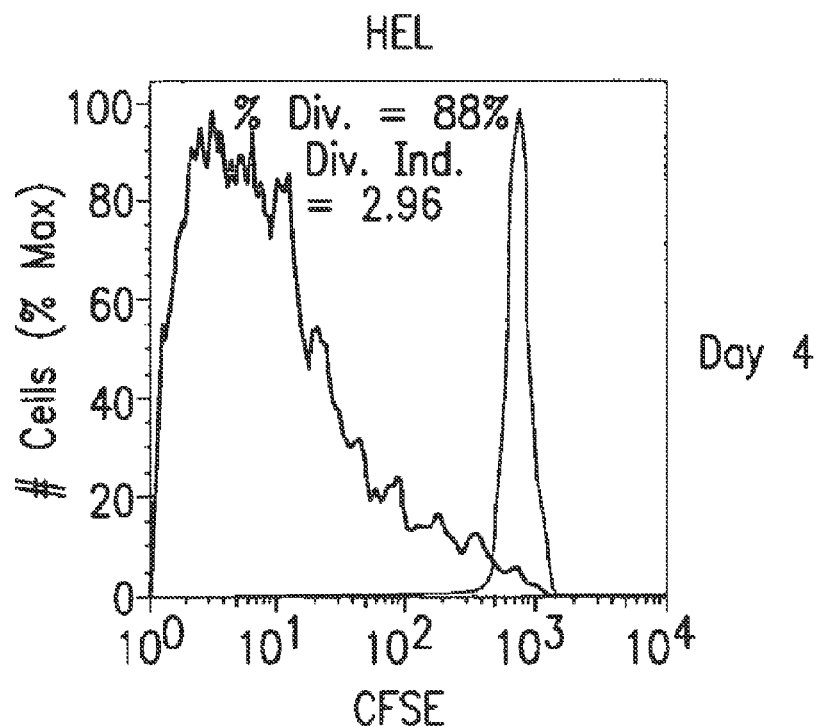
Figure 6D:
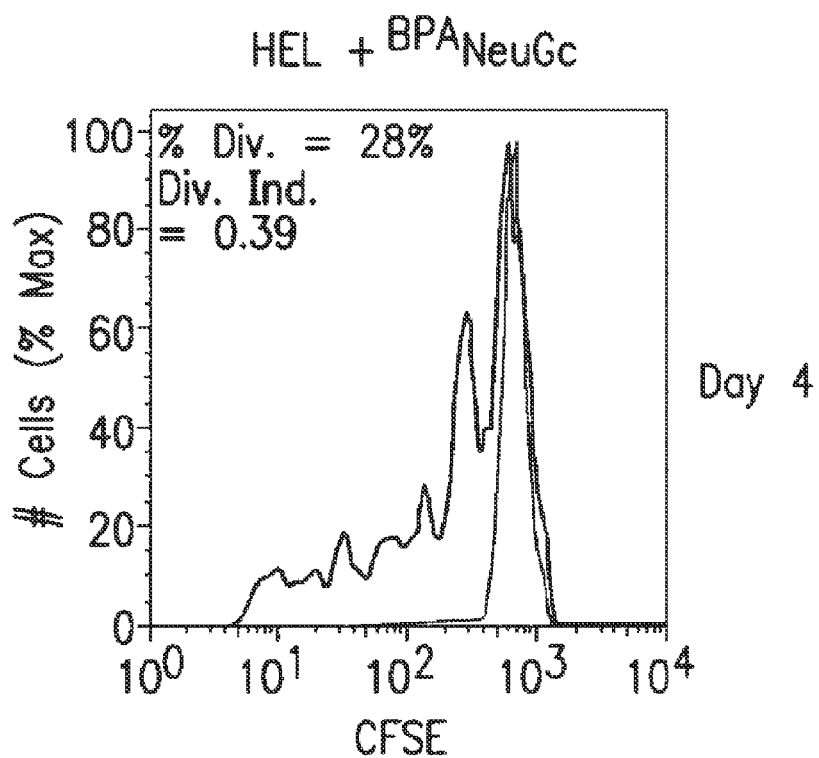

We next examined whether co-presentation of $^{BPA}$NeuGc and HEL on liposomes can reduce the proliferation of HEL-specific B cells in vitro, HEL-specific B cells were purified from the spleen of MD4 mice and fluorescently labeled with carboxyfluorescein succinimidyl ester (CFSE). Liposomes (10 nM final concentration) displaying HEL alone (FIGS. 4A, 4C, 4E) or HEL and $^{BPA}$NeuGc (FIGS. 4B, 4D, 4F) were incubated with 2×10$^5$ cells. Some cells were not treated with any liposomes. Using flow cytometry, the dilution of CFSE signal in the cells was monitored on the indicated days. Cells treated without liposomes are shown in shaded grey in order to establish the position of the undivided cells. Indicated on each graph is the percentage of divided cells and the division index, which is the average number of cell divisions that cells in the original population have undergone. The results as shown in Wis. 4A-4F indicate that co-presentation of $^{BPA}$NeuGc and HEL on liposomes greatly reduced the proliferation of HEL-specific B cells in vitro.

We further assessed whether co-presentation of $^{BPA}$NeuGc and HEL on liposomes can leads to apoptosis of HEL-specific B cells in vitro. HEL-specific B cells were purified from the spleen of MD4 mice, Liposomes (10 nM final concentration) displaying HEL alone (FIG. 5A) or HEL, and $^{BPA}$NeuGc (FIG. 5B) were incubated with 2×10$^5$ cells. Some cells were not treated with any liposomes. After two days of incubation, the extent of apoptosis was determined by staining the cells with AnnexinV-FITC and analysis by cytometry. For each graph, cells treated without liposomes are shown in shaded grey. The results from the study are shown in FIG. 5A-5B. As shown in the figure, co-presentation of $^{BPA}$NeuGc and HEL on liposomes causes apoptosis of HEL-specific B cells in vitro.

We additionally studied whether co-presentation of $^{BPA}$NeuGc and HEL, on liposomes greatly reduces the proliferation of HEL-specific B cells in vivo. In the study, HEL-specific B cells were purified from the spleen of MD4 mice (wild-type or CD22 knockout background) and fluorescently labeled with carboxyfluorescein succinimidyl ester (CFSE), Labeled cells (8×10$^6$ or 5×10$^6$) were transferred into a host C57BL/6J mouse via the tail vein. Two hours later, liposomes displaying HEL alone or HEL and $^{BPA}$NeuGc were injected via the tail vein. Several mice were injected with buffer as a control. On the indicated day, the spleen was removed and dilution of CFSE signal in spleenocytes was determined by flow cytometry, HEL-specific B cells were gated for by staining with an anti-IgM$^a$-PE antibody. Mice injected with buffer are shown in shaded grey in order to establish the position of the undivided cells. Indicated on each graph is the percentage of divided cells and the division index, which is the average number of cell divisions that cells in the original population have undergone. The results obtain the study, shown in FIG. 6A-6D, indicate that co-presentation of $^{BPA}$NeuGc and HEL on liposomes also greatly reduces the proliferation of HEL-specific B cells in vivo. Repeating this experiment with HEL-specific B cells on a CD22 deficient background resulted in no difference between the liposomes with or without BPANeuGc, indicating that the effect is entirely CD22-dependent.

Figure 7A:
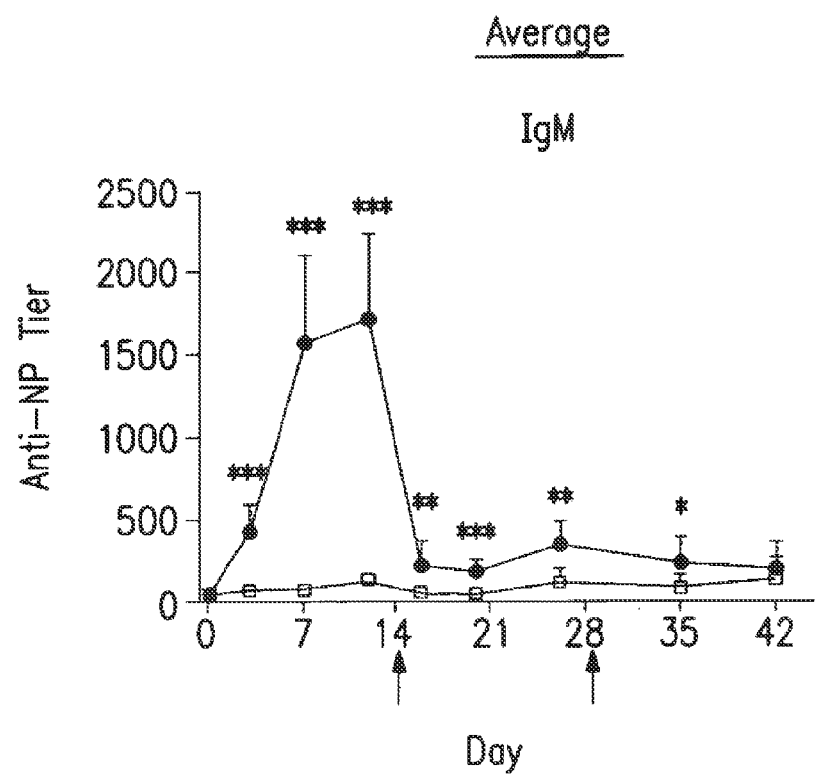
FIGS. 7A-7D show that liposomes displaying BPANeuGc and nitrophenyl (NP) induces tolerance to NP in mice. Liposomes (2.5 mM lipid) displaying NP alone (filled circles) or $^{BPA}$NeuGc and NP (open squares injected (at day 0) into C57BL/6J mice (n=10 per group) via the lateral tail vein. On various days, the mice were bled and the anti-NP titer (IgM and IgG isotypes) was determined by an ELISA assay. On days 14 and 28 of the experiment (indicated with the arrows), both groups were challenged with liposomes displaying NP alone.
Figure 7B:
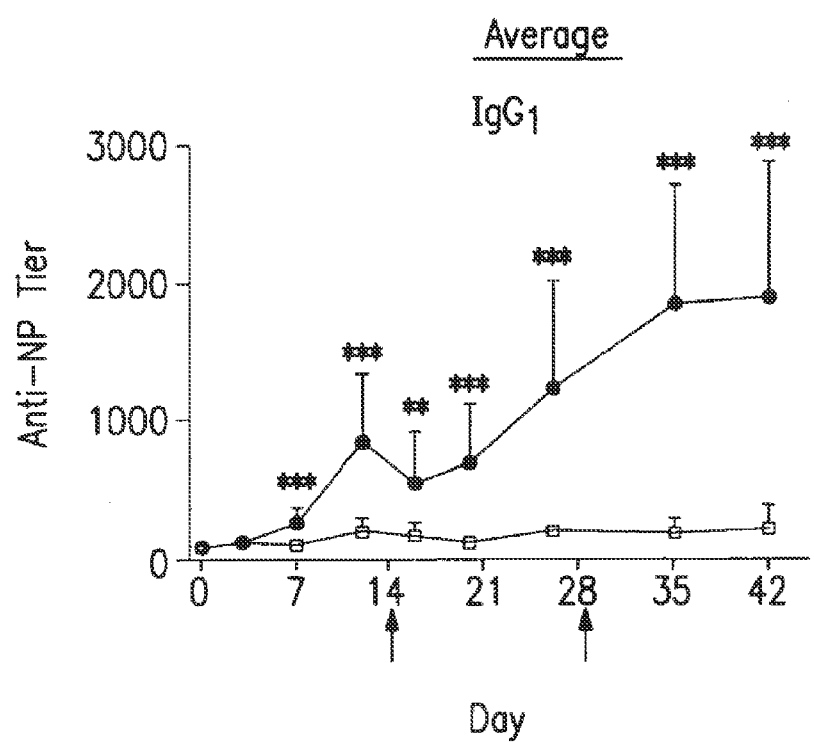
Figure 7C:
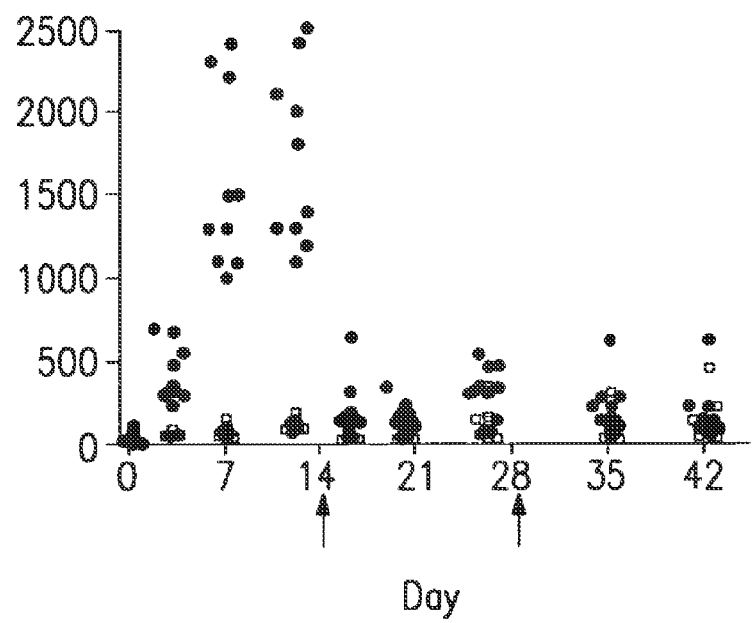
Figure 7D:
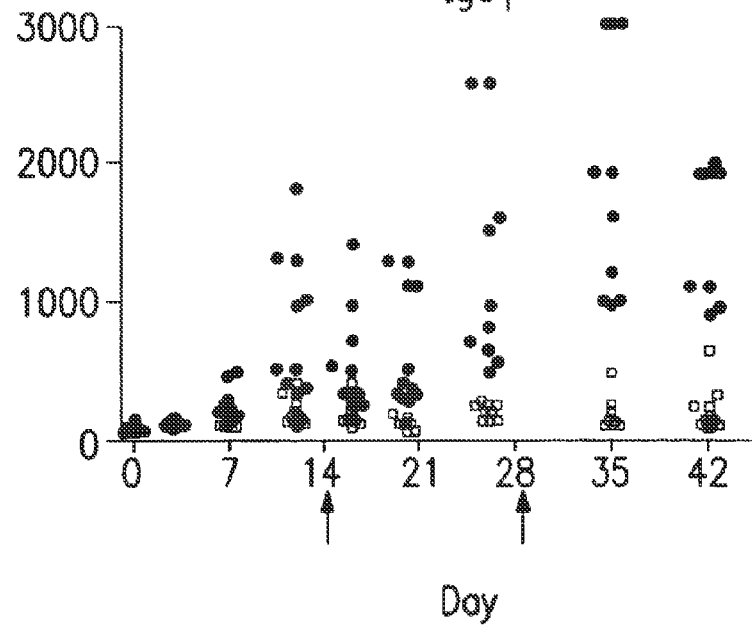

Finally, we examined whether liposomes displaying $^{BPA}$INeuGc and nitrophenyl (NP) can also induce tolerance to NP in mice. Specifically, on day 0, 200 μL of liposomes (2.5 niM lipid) displaying NP alone (filled circles) or $^{BPA}$NeuGc and NP (open squares) were injected into C57BL/6J mice (n=10 per group) via the lateral tail vein. On various days, the mice were bled and the anti-NP titer (IgM and IgG isotypes) was determined by an EL1SA assay. On days 14 and 28 of the experiment (indicated with the arrows), both groups were challenged with liposomes displaying NP alone. Shown in FIGS. 7A-7B are average values and in FIGS. 7C-7D scatter plots [plot] containing each individual data point. Statistical significance between the two groups at each time point is noted by the asterisks (*p<0.05; p<0.01; *p<0.001). The data obtained from the study (FIGS. 7A-7D) show that liposomes displaying $^{BPA}$NeuGc and nitrophenyl (NP) induces tolerance to NP in mice.

* * *

The invention thus has been disclosed broadly and illustrated in reference to representative embodiments described above. It is understood that various modifications can be made to the present invention without departing from the spirit and scope thereof. It is further noted that all publications, patents and patent applications cited herein are hereby expressly incorporated by reference in their entirety and for all purposes as if each is individually so denoted. Definitions that are contained in text incorporated by reference are excluded to the extent that they contradict definitions in this disclosure.

The invention claimed is:

1. A method for suppressing or preventing an immune response to a specific antigen in a subject, comprising administering to the subject a pharmaceutical composition comprising a liposome composition displaying the antigen and a ligand for a sialic acid binding Ig-like lectin (Siglec).

2. The method of claim 1, wherein the antigen is an autoantigen.

3. The method of claim 1, wherein the Siglec is a Siglec expressed on monocytes or macrophages.

4. The method of claim 1, wherein the Siglec is a Siglec expressed on B lymphocytes.

5. The method of claim 4, wherein the Siglec is CD22 or Siglec- G/10.

6. The method of claim 1, wherein the subject is a human.

7. The method of claim 6, wherein the Siglec ligand is 9-N-biphenylcarboxyl-NeuAcα2-Galβ1-4GlcNAc (6'-BPC-NeuAc), NeuAcα2-6Galβ1-4GlcNAc, or NeuAcα2-6Galβ1-4(6-sulfo)GlcNAc.

8. The method of claim 1, wherein the antigen is an allergen, or an alloantigen.

* * * * *

UNITED STATES PATENT AND TRADEMARK OFFICE
CERTIFICATE OF CORRECTION

PATENT NO. : 9,981,023 B2
APPLICATION NO. : 15/370313
DATED : May 29, 2018
INVENTOR(S) : Paulson et al.

It is certified that error appears in the above-identified patent and that said Letters Patent is hereby corrected as shown below:

On the Title Page

In item (*), in "Notice", in Column 1, Line 3, delete "days. days." and insert --days.-- therefor In the Specification In Column 2, Line 25, delete "liposome," and insert --liposome.-- therefor In Column 2, Line 45, delete "macrophages," and insert --macrophages.-- therefor In Column 3, Line 5, delete "liposomes," and insert --liposomes.-- therefor In Column 3, Line 39, delete "HEIL" and insert --HEL-- therefor In Column 3, Line 43, delete "vitro," and insert --vitro.-- therefor In Column 3, Line 47, delete "BPANeuGc" and insert --$^{BPA}$NeuGc-- therefor In Column 3, Line 52, delete "BPANeuGc" and insert --$^{BPA}$NeuGc-- therefor In Column 3, Lines 55-56, delete "BPANeuGc" and insert --$^{BPA}$NeuGc-- therefor In Column 3, Line 59, delete "BPANeuGc" and insert --$^{BPA}$NeuGc-- therefor In Column 3, Line 64, delete "BPANeuGc" and insert --$^{BPA}$NeuGc-- therefor In Column 4, Line 4, delete "BPANeuGc" and insert --$^{BPA}$NeuGc-- therefor In Column 4, Line 28, delete "BPANeuGc" and insert --$^{BPA}$NeuGc-- therefor Signed and Sealed this
Eleventh Day of June, 2019

Andrei Iancu
*Director of the United States Patent and Trademark Office*

CERTIFICATE OF CORRECTION (continued)
U.S. Pat. No. 9,981,023 B2

In Column 4, Line 31, delete "squares" and insert --squares) were-- therefor

In Column 5, Line 33, after "Dictionary", insert --of--

In Column 6, Line 22, delete "cell" and insert --T cell-- therefor

In Column 6, Line 33, delete "Where" and insert --where-- therefor

In Column 6, Line 61, delete "structure," and insert --structure.-- therefor

In Column 8, Line 39, delete "methods, in" and insert --methods. In-- therefor

In Column 10, Line 38, delete "2007/05625;" and insert --2007/056525;-- therefor In Column 10, Line 42, delete "CE22" and insert --CD22-- therefor In Column 11, Lines 34-35, delete "ethanol amine" and insert --ethanolamine-- therefor In Column 12, Line 15, delete "conjugates," and insert --conjugates.-- therefor In Column 12, Line 57, delete "a." and insert --a-- therefor In Column 13, Line 59, delete "art ," and insert --art,-- therefor In Column 14, Line 40, delete "instructions" and insert --Instructions-- therefor In Column 15, Line 48, delete "vitro," and insert --vitro.-- therefor In Column 15, Line 61, delete "Wis." and insert --FIGS.-- therefor In Column 16, Line 1, delete "mice," and insert --mice.-- therefor In Column 16, Line 25, delete "cytometry," and insert --cytometry.-- therefor In Column 16, Line 38, delete "BPANeuGc," and insert --$^{BPA}$NeuGc,-- therefor In Column 16, Line 43, delete "niM" and insert --mM-- therefor In Column 16, Line 47, delete "EL1SA" and insert --ELISA-- therefor